United States Patent
Kalow et al.

(10) Patent No.: US 11,820,870 B2
(45) Date of Patent: Nov. 21, 2023

(54) PHOTOCONTROLLED DYNAMIC COVALENT LINKERS FOR POLYMER NETWORKS

(71) Applicant: Northwestern University, Evanston, IL (US)

(72) Inventors: Julia A. Kalow, Evanston, IL (US); Joseph V. Accardo, Ft. Myers, FL (US); Boyeong Kang, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 17/840,934

(22) Filed: Jun. 15, 2022

(65) Prior Publication Data

US 2022/0306816 A1    Sep. 29, 2022

Related U.S. Application Data

(62) Division of application No. 17/055,777, filed as application No. PCT/US2019/032881 on May 17, 2019, now Pat. No. 11,401,387.

(60) Provisional application No. 62/673,312, filed on May 18, 2018.

(51) Int. Cl.
| | | |
|---|---|---|
| C08F 2/46 | (2006.01) | |
| C08F 2/50 | (2006.01) | |
| C08G 61/04 | (2006.01) | |
| C08J 3/075 | (2006.01) | |
| C08J 3/24 | (2006.01) | |
| C08J 3/28 | (2006.01) | |
| C08K 5/55 | (2006.01) | |
| C08L 5/04 | (2006.01) | |
| C08L 5/08 | (2006.01) | |
| C08L 71/02 | (2006.01) | |
| C08L 89/00 | (2006.01) | |

(52) U.S. Cl.
CPC ............ *C08J 3/075* (2013.01); *C08J 3/24* (2013.01); *C08J 3/28* (2013.01); *C08K 5/55* (2013.01); *C08L 5/04* (2013.01); *C08L 5/08* (2013.01); *C08L 71/02* (2013.01); *C08L 89/00* (2013.01); *C08J 2305/04* (2013.01); *C08J 2305/08* (2013.01); *C08J 2371/02* (2013.01); *C08J 2389/00* (2013.01); *C08L 2203/02* (2013.01); *C08L 2312/06* (2013.01)

(58) Field of Classification Search
CPC .. C08L 5/04; C08L 89/00; C08L 71/02; C08L 2203/02; C08L 2312/06; A61K 74/34; C08K 5/55; C08J 3/24; C08J 3/28; C08J 3/246; C08J 3/075; C08J 2371/02; C08J 2305/08; C08J 2305/04; C08J 2489/00; C08J 2300/208; C08J 2389/00
USPC ............... 522/62, 71, 1, 189, 184, 6; 520/1
See application file for complete search history.

(56) References Cited

U.S. PATENT DOCUMENTS 11,401,387 B2 * 8/2022 Kalow ................ C08L 5/08

OTHER PUBLICATIONS

Accardo et al, Reversibly tuning hydrogel stiffness through photocontrolled dynamic covalent crosslinks, Jun. 19, 2018, Cem. Sci., 9, 5987-5993 (Year: 2018).*

* cited by examiner

*Primary Examiner* — Jessica Whiteley
(74) *Attorney, Agent, or Firm* — Bell & Manning, LLC

(57) ABSTRACT

Reversibly crosslinkable polymeric networks, including reversibly crosslinkable hydrogel networks are provided. Also provided are methods of making the polymeric networks and methods of using the hydrogel networks in tissue engineering applications. The reversibly crosslinkable polymeric networks are composed of polymer chains that are covalently crosslinked by azobenzene boronic ester bonds that can be reversibly formed and broken by exposing the polymeric networks to different wavelengths of light.

19 Claims, 16 Drawing Sheets

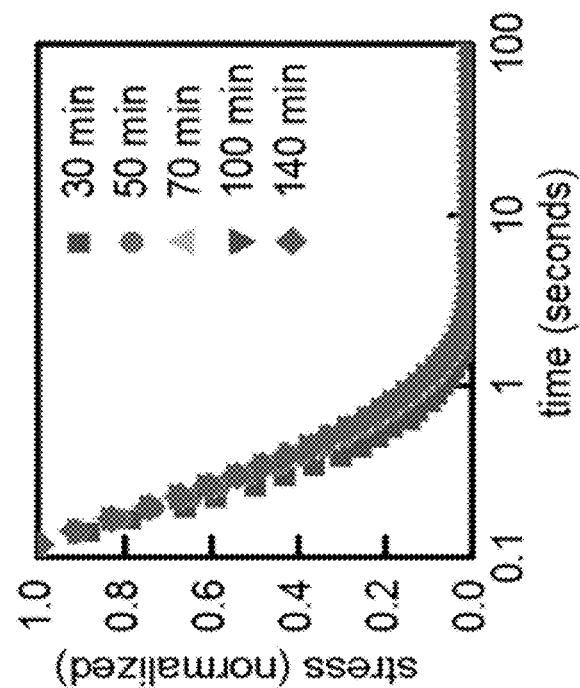
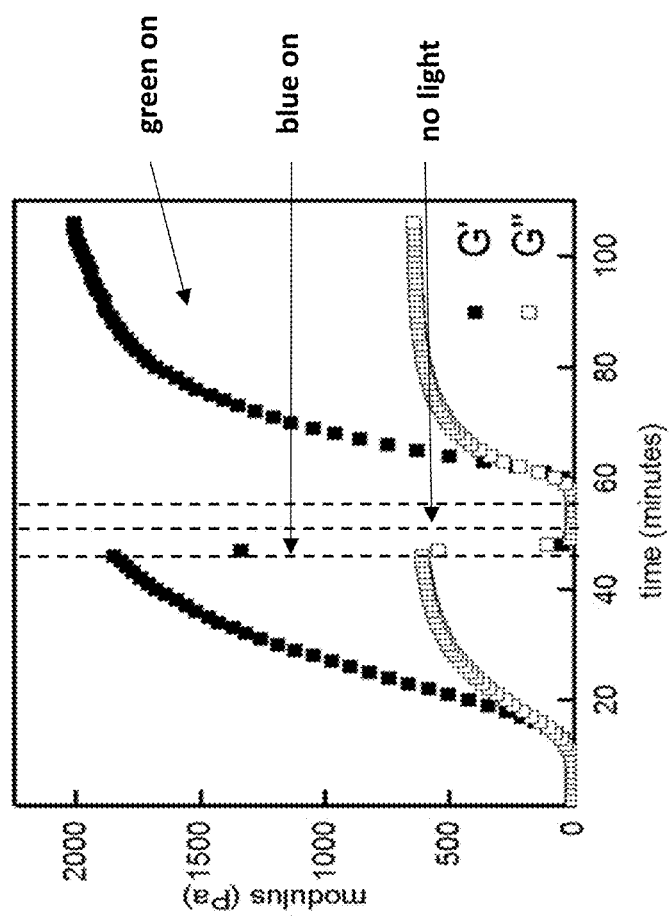
FIG. 10B
FIG. 10A

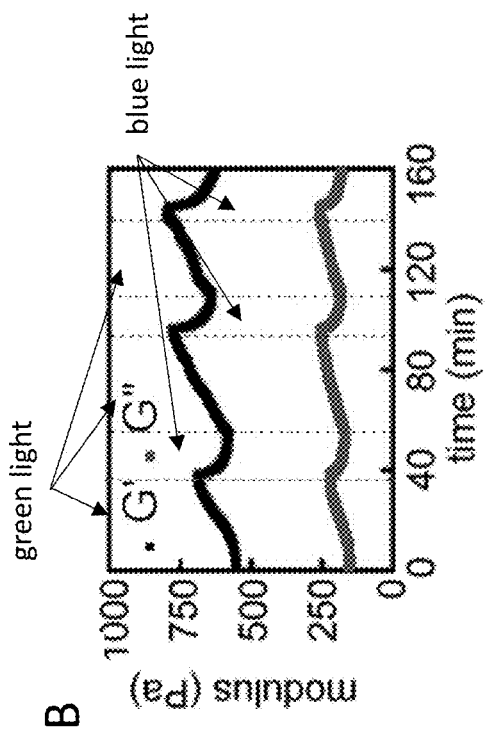
FIG. 11A
FIG. 11B
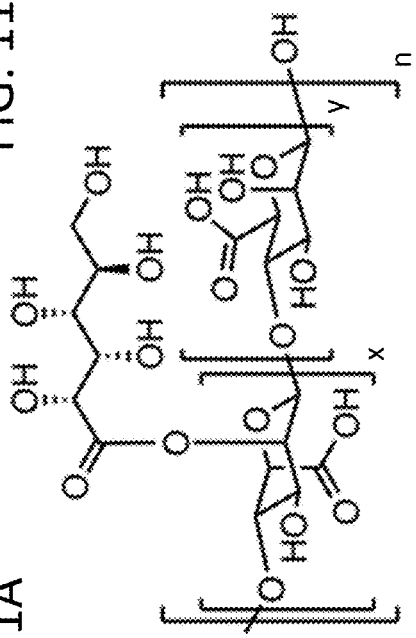
FIG. 11C

PHOTOCONTROLLED DYNAMIC COVALENT LINKERS FOR POLYMER NETWORKS

CROSS-REFERENCE TO RELATED APPLICATIONS

The present application is a divisional application of U.S. patent application Ser. No. 17/055,777 filed Nov. 16, 2020, which claims priority as a National Stage Application of International Application number PCT/US19/32881 filed May 17, 2019, which claims the priority benefit of U.S. patent application Ser. No. 62/673,312, filed May 18, 2018, the contents of all of which are incorporated by reference herein in their entirety.

BACKGROUND

Polymer networks crosslinked with dynamic bonds can be self-healing, adaptive, and recyclable. The conditions under which these properties are observed depend on the stability and lifetime of the dynamic bonds. By tailoring crosslink stability and reactivity, macroscopic properties can be programmed at the molecular level. Furthermore, if changes in crosslink density or dynamics occur in response to a stimulus, these materials exhibit tunable macroscopic properties. External stimuli such as pH, temperature, and magnetic field have been employed to reversibly tune the properties of dynamic polymer networks.

As soft materials with mechanics and water content that approximate those of tissues, hydrogels benefit from the introduction of reversible, externally controlled properties. While traditional stimuli such as pH or temperature present limitations on biocompatibility, light (particularly in the visible to near-infrared (IR) range) represents an ideal stimulus. Light can be applied externally with precise spatial and temporal control, at controlled wavelengths and fluxes. However, the majority of photocontrolled hydrogels rely on irreversible photochemical reactions, such as photoinitiated radical polymerization for stiffening or o-nitrobenzyl cleavage for softening. In addition to their irreversibility, these reactions require exogenous reagents or release byproducts into the hydrogel matrix.

Reversible light-responsive hydrogels are comparatively rare due to the limited number of photoreversible reactions that can be coupled to a change in hydrogel stiffness. Covalently linked hydrogels based on photoreversible [2+2] cycloadditions display reversible stiffening and softening at low concentrations. While recent work has achieved the cycloaddition with visible light, the reverse reaction invariably requires ultraviolet (UV) irradiation. As an alternative to photoreversible reactions, many researchers have turned to the photoswitch azobenzene, which undergoes reversible E/Z isomerization in response to two different wavelengths of light. Rosales and coworkers enchained azobenzene in an elastic network and observed small but reproducible changes in stiffness. (See, Rosales et al., *Biomacromolecules.* 2015, 16, 798.) Notably, the above systems are not dynamic in the absence of light; these elastic networks store, rather than dissipate, energy from applied strain. To achieve a sol-gel transition in a stress-relaxing network, Harada and coworkers designed a supramolecular hydrogel based on cyclodextrin/azobenzene complexes that has been leveraged in multiple contexts. (See, Tamesue et al., *Angew. Chem. Int. Ed.* 2010, 49, 7461; Tomatsu, et al., *J. Am. Chem. Soc.* 2006, 128, 2226; and Yamaguchi et al., *Nat. Commun.* 2012.)

SUMMARY

Reversibly photo-crosslinkable polymeric networks, including reversibly photo-crosslinkable hydrogel networks, are provided. Also provided are cell culture scaffolds and hybrid hydrogel materials made from the photo-crosslinkable polymeric networks, as well as methods for using the cell culture scaffolds in tissue engineering applications.

One embodiment of a hydrogel includes a crosslinked polymer network comprising covalent azobenzene boronic ester crosslinks between the organic polymer backbone chains.

One embodiment of a cell culture scaffold includes: a hydrogel comprising a crosslinked polymer network comprising covalent azobenzene boronic ester crosslinks between the organic polymer backbone chains; and biological cells seeded on the hydrogel or encapsulated in the hydrogel.

One embodiment of a hybrid hydrogel material includes: a hydrogel comprising a crosslinked polymer network comprising covalent azobenzene boronic ester crosslinks between the organic polymer backbone chains; and a fiber-forming biomaterial, wherein the hydrogel and the fiber-forming biomaterial form an interpenetrating network.

Another embodiment of a cell culture scaffold includes: a hybrid hydrogel material and biological cells seeded on the hybrid hydrogel material or encapsulated in the hybrid hydrogel material. The hybrid hydrogel material includes: a hydrogel comprising a crosslinked polymer network comprising covalent azobenzene boronic ester crosslinks between the organic polymer backbone chains; and a fiber-forming biomaterial, wherein the hydrogel and the fiber-forming biomaterial form an interpenetrating network.

The polymer networks, including the hydrogels can be formed from a reversibly crosslinkable composition that includes: a first molecule comprising at least two terminal azobenzene boronic acid groups; and a second molecule comprising at least two terminal diol groups, provided that at least one of the first and second molecules is a polymer, and further provided that, if the first molecule has only two terminal azobenzene boronic acid groups, then the second molecule comprises at least three terminal diol groups, and if the second molecule has only two terminal diol groups, the first molecule has at least three terminal azobenzene boronic acid groups; wherein the first molecule is characterized in that its azobenzene groups undergo a reversible E to Z isomerization upon irradiation with ultraviolet light, visible light, or infrared light, and its boronic acid groups react with the terminal diol groups of the second polymer to form a polymer network comprising covalent azobenzene boronic ester bonds.

BRIEF DESCRIPTION OF THE DRAWINGS

Illustrative embodiments of the invention will hereafter be described with reference to the accompanying drawings.

FIG. 9A shows the UV-induced gelation profile of P1 and P2 (1:1, 10 w/v % in PBS, pH 7.5, 10% strain, 25 rad/s). FIG. 9B depicts the photocontrolled cycling of hydrogel viscoelasticity (10% strain, 25 rad/s). UV light induces gelation, which is reversed with blue light. UV light is required to re-initiate stiffening of the gel. FIG. 9C shows the dynamic frequency sweep measurements as a function of irradiation (10% strain). Inset: stress relaxation of the hydrogel (gelled for 60 minutes) after applying 10% strain.

FIG. 10A depicts the photocontrolled cycling of hydrogel viscoelasticity (10% strain, 25 rad/s) of P1 and P2-$F_2$ (1:1, 10 w/v % in PBS, pH 7.5). Green light induces gelation, and blue light induces softening. FIG. 10B shows the stress-relaxation of the gel as a function of irradiation time.

FIG. 11A depicts the structure of a diol-grafted alginate. The diol-grafted alginate was combined with a telechelic bis-azobenzene boronic acid linker, and the resulting alginate gels were photoresponsive (FIG. 11B) and exhibited slower stress relaxation than P1 gels with the same linker (FIG. 11C).

DETAILED DESCRIPTION

Reversibly photo-crosslinkable polymeric networks, including reversibly photo-crosslinkable hydrogel networks, are provided. Also provided are methods of making the polymeric networks and methods of using the hydrogel networks in tissue engineering applications.

The hydrogel networks are viscoelastic; like natural tissues, they have solid-like and liquid-like characteristics. Photocontrolled dynamic crosslinkers in hydrogel networks allow for rational spatiotemporal tuning of the mechanical properties and biochemical content of the materials, rendering the materials useful as synthetic biomaterials. The rational tuning of the gel viscoelasticity with light enables the synthesis of gels having a range of mechanical properties, including physiologically relevant mechanical properties. Because the viscoelastic properties of the gels can be controlled both temporally and spatially, the gels have the ability to mimic biological tissues, such as the ECM, which have heterogenous mechanical properties that can change over time.

The reversibly crosslinkable polymeric networks are composed of polymer chains that are covalently crosslinked by azobenzene boronic ester crosslinks. The azobenzene boronic ester crosslinks are dynamic covalent crosslinks that can be reversibly formed and broken by exposing the polymeric networks to different wavelengths of UV, visible, and/or IR light. As a result, the density of crosslinks and the viscoelastic properties of the polymeric networks can be tailored by exposure light. The stiffness (G', storage modulus) of the crosslinked gels increases as a function of irradiation time and, therefore, the viscoelastic properties of the gels can be externally tailored by controlling the irradiation time. Notably, this external tuning of the hydrogel stiffness can be achieved independent of stress relaxation. This is significant for tissue engineering applications because substrate stiffness and substrate stress relaxation can independently control cell fate.

The polymeric networks and gels can be formed from compositions that include a mixture of a first molecule having at least two reactive terminal azobenzene boronic acid groups—that is, terminal boronic acid-substituted azobenzene groups—and a second molecule having at least two reactive terminal diol groups, wherein at least one of the two molecules has at least three of its respective reactive terminal groups.

Figure 1A:
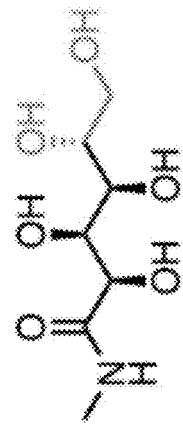
FIG. 1A shows an illustrative example of an azobenzene boronic acid end group.
Figure 1B:
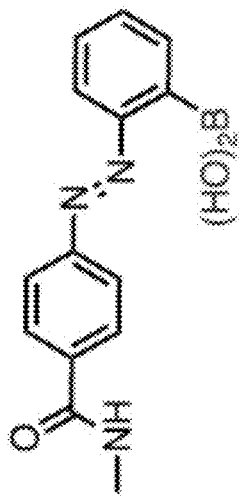
FIG. 1B shows an illustrative example of a diol group-containing end group.

The external control of the mechanical properties of the gels is provided by the small-molecule azobenzene boronic acid and —OH end groups, which can be installed on any synthetic or biological molecule or polymer of interest. An illustrative example of an azobenzene boronic acid group is shown in FIG. 1A and an illustrative example of a diol group-containing end group is shown in FIG. 1B.

Figure 1C:
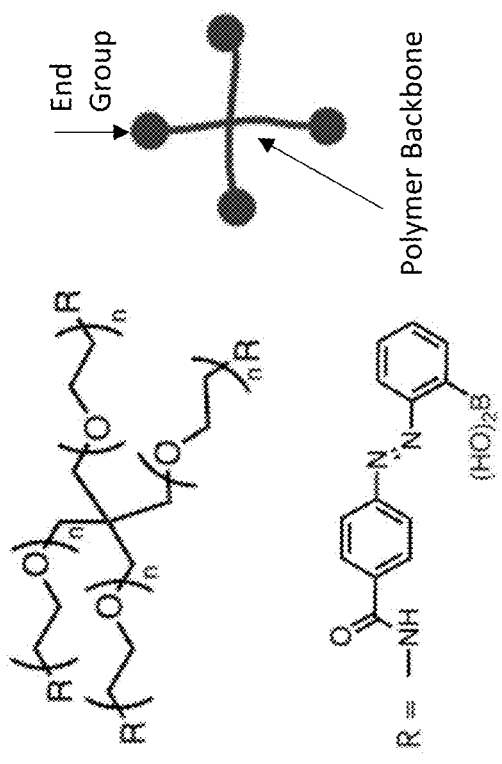
FIG. 1C shows the chemical structure (left) and a schematic representation (right) of one example of a branched polymer having diol end groups.
Figure 1D:
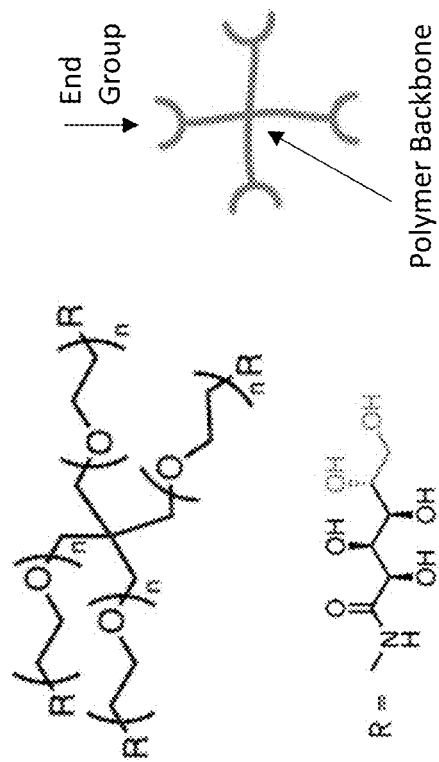
FIG. 1D shows the chemical structure (left) and a schematic representation (right) of one example of a branched polymer having azobenzene boronic acid end groups.

The molecules bearing the azobenzene boronic acid and diol end groups can be small molecules or polymers. As used herein, the term polymers encompasses oligomers which are comprised of only a relatively few repeat units, for example, 3-5 repeat units. In some embodiments, at least one of the two molecules is a polymer. For example, the molecule having at least three reactive terminal groups may be a branched polymer. In some embodiments, both the first and the second molecules are branched polymers. The chemical structure (left) and a schematic representation (right) of one example of a branched polymer having diol end groups is shown in FIG. 1C, and the chemical structure (left) and a schematic representation (right) of one example of a branched polymer having azobenzene boronic acid end groups is shown in FIG. 1D. For purposes of illustration, both polymers are polyethylene glycol polymers in FIGS. 1C and 1D. However, other polymers can be used, as discussed in more detail below, and the polymer that forms the backbone of the diol group-bearing polymer need not be the same polymer that forms the backbone of the azobenzene boronic acid group-bearing polymer.

Figure 1F:
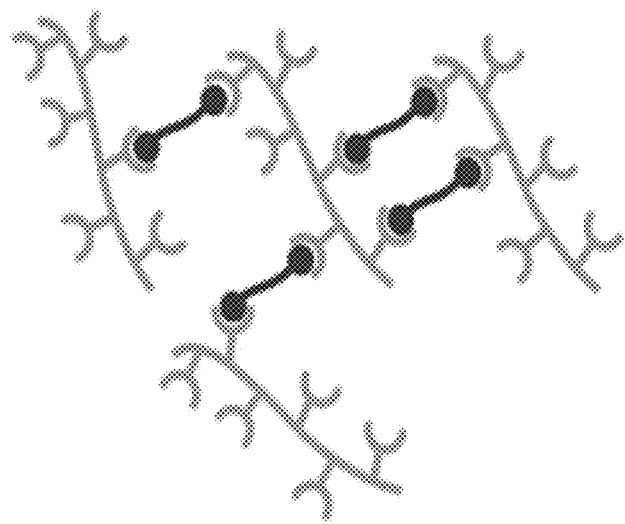
FIG. 1F shows molecular crosslinks between polymer chains of a first polymer.
Figure 1E:
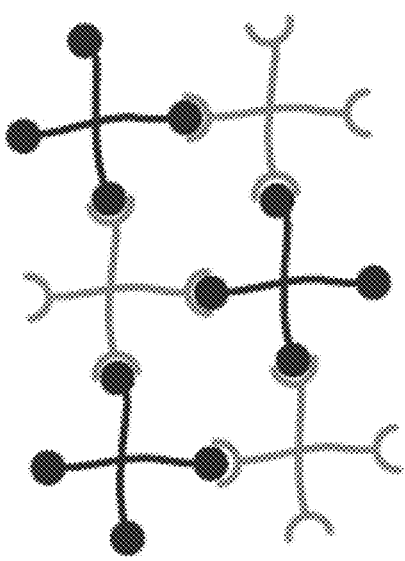
FIG. 1E shows crosslinks between a first polymer and a second polymer.

Crosslinks are formed between polymer chains in the composition when the boronic acid substituents react with the diol groups. The crosslinks may be between the first molecule and the second molecule if both molecules are polymers; this is illustrated schematically in FIG. 1E. Alternatively, if only one of the first and second molecules is a polymer, the crosslinks can be formed between polymer chains of that polymer, as shown schematically in FIG. 1F. In these systems, the equilibrium of the reaction between the azobenzene boronic acid groups and diol groups to form the boronic ester is controlled by the configuration of the azobenzene groups, which act as photoswitches for the reaction.

Although the azobenzene-group-containing molecules may have only two terminal azobenzene boronic acid groups, they may also have more than two such groups. For example, the molecules may be tri- or higher functional small molecules or branched polymers having at least three or at least four azobenzene boronic acid groups. Similarly, the diol-group-containing molecules may have only two terminal diol groups, but they may also have more than two such groups. For example, these molecules also may be tri- or higher functional small molecules or branched polymers having at least three or at least four terminal diol groups. A variety of molecules can be used in the compositions including synthetic and naturally occurring polymers, provided they can be functionalized with azobenzene boronic acid groups or diol groups.

Figure 2:
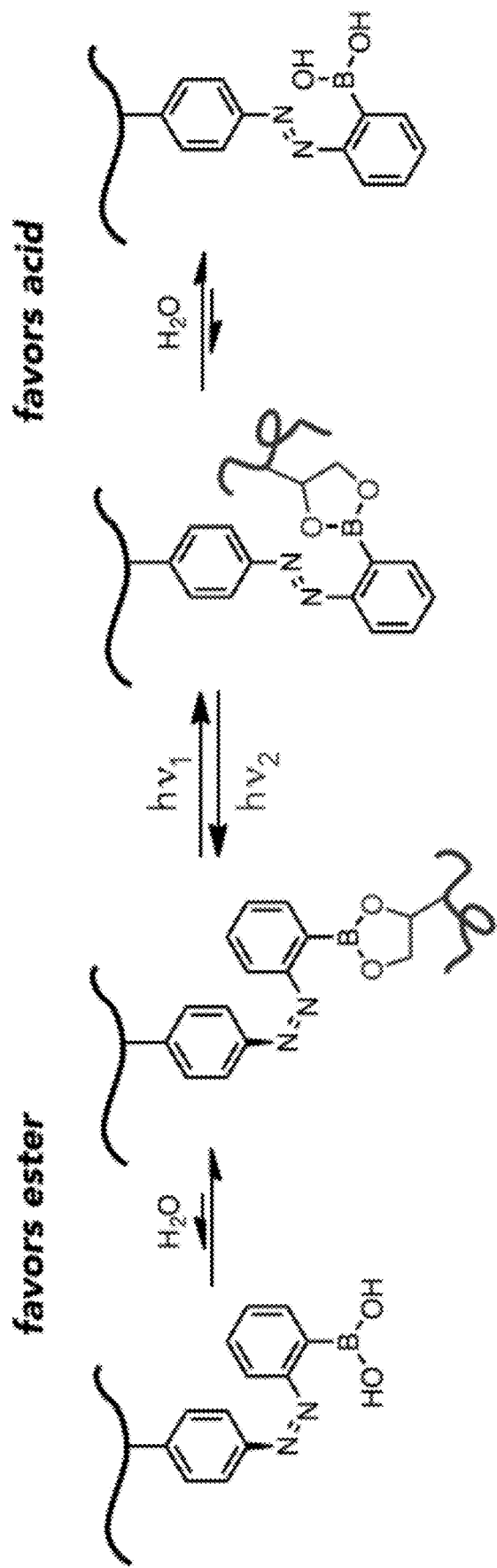
FIG. 2 shows the reversible crosslinking of a polymer network using azobenzene boronic acid functionalities.

The reversible crosslinking of a polymer network using azobenzene boronic acid functionalities is illustrated in FIG. 2. When the azobenzene group is in its E form (right panel), the equilibrium in an aqueous dispersion favors the boronic acid and crosslinking is disfavored. However, when the azobenzene group is in its Z form (left panel), boronic ester crosslink formation is favored. The isomerization from the E form to the Z form of the azobenzene group can be induced by exposing the molecules (e.g., polymers) to UV light, visible light, or IR light, including near-IR ($hv_2$), while the reverse isomerization from the Z form to the E form can be induced by exposing the resulting network to a different wavelength of visible and/or UV light, including blue light ($hv_1$). As a result, upon irradiating a mixture of molecules functionalized with azobenzene-boronic acids and diols with two different wavelengths of light, crosslinks in the covalent network can be formed and re-broken. These cycles can be performed repeatedly.

In some embodiments of the compositions, the polymer network that forms upon crosslinking is a highly crosslinked gel, such as a hydrogel. If hydrogel formation is desired, the polymers used to form the crosslinked network should be hydrogel-forming polymers, such as poly(ethylene) glycol polymers. Other hydrogel forming polymers include natural polymers, such as glycosamineglycans, including hyaluronic acid, polysaccharides, such as alginate, gelatin, and dextran, and synthetic polymers, such as polyvinylalcohol, polyacrylamides, polyesters, and polyacrylates. These and other polymers can be modified to incorporate diol groups using known chemistries. By way of illustration, a ring-opening reaction of δ-gluconolactone with the polymer can be used to form a water-soluble, unhindered pentaol-grafted polymer, which can be reacted with an azobenzene boronic acid crosslinker to form a gel. The modification of alginate with diol-bearing end groups is illustrated in Example 2.

In addition, it may be desirable to use polymers having three or more terminal azobenzene boronic acid groups. The hydrogels may be formed from a starting composition that is a hydrosol, such that sequential exposure of the composition to two different wavelengths of light induces a reversible sol-gel transition. However, the initial composition may also undergo some initial crosslinking to form a hydrogel, in which case, the sequential exposure of the composition to two different wavelengths of light induces a stiffening and then softening of the hydrogel.

Figure 3:
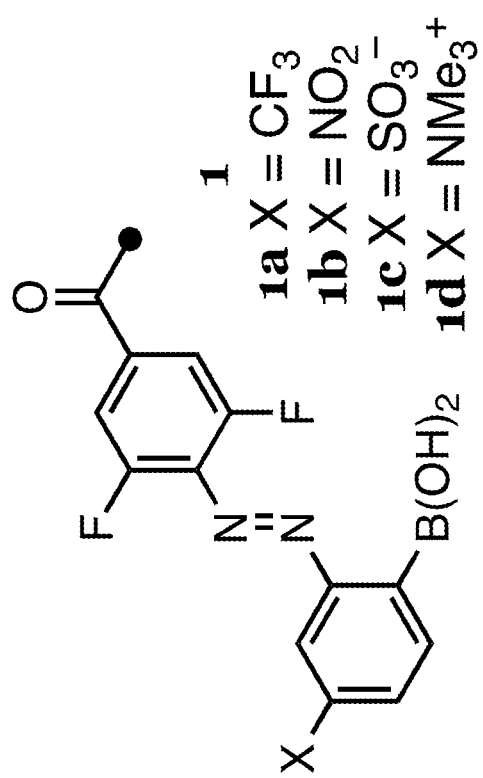
FIG. 3 depicts structural modifications to an azobenzene boronic acid crosslinking group. The black dot represents the attachment point of the end groups to the polymer backbone.

Mechanical properties of the gels, such as stiffness and stability, can be adjusted by chemical modifications to the azobenzene groups. For example, an azobenzene ring having fluoride substitutes, such as o-difluoroazobenzene, can be used to provide a higher binding affinity between the azobenzene boronic acid and the diols. Also, crosslinking can be promoted and, therefore, gel stiffness increased by incorporating electron-withdrawing groups on the azobenzene group. Electron withdrawing groups, such as $CF_3$, $NO_2$, $SO_3^-$, and $NMe_3^+$, para to the boronic ester group will favor boronic ester crosslink formation, due to the increased Lewis acidity of the boronic acid group. Examples of azobenzene boronic acid end groups are shown in FIG. 3.

One way to extend the lifetime of the dynamic covalent hydrogels to days-weeks, while maintaining stress relaxation, is to incorporate a small percentage of permanent crosslinks in the gels. This percentage can be a percentage above the gel point, as determined by the Carothers or Flory-Stockmayer approximations. In various embodiments of the gels, the mole percent of monomers that form permanent crosslinks can be in the range of, for example, 0.1% to 20%, including in the range of 1% to 10%. However, higher or lower mole percent ranges can be used.

The resulting hydrogels are viscoelastic but do not relax stress fully or dissolve. Azide-alkyne, thiol-ene, and/or amide functionalities are examples of functionalities that can be incorporated into one or both of the molecules/polymers that make up the gels to provide permanent crosslinking.

The properties of the gels can also be modulated by the relative amount of the two molecules (e.g., polymers) in the compositions, which can be varied over a relatively wide range. By tuning the ratio of the two molecules, the gel stability and/or photoresponse can be modulated. By way of illustration, the weight ratio of the first molecule to the second molecule in some embodiments of the compositions is in the range from about 1:2 to about 2:1, including within the range from about 1:1.5 to 1.5:1. However, weight ratios outside of this range can also be used.

As illustrated in the Example, the hydrogels can be viscoelastic, exhibiting stress relaxation on the order of seconds (e.g., half-life, $t_{1/2} \leq 100$ seconds), and the stiffness can be tuned independently of the crossover frequency. Some embodiments of the hydrogels have a maximum storage modulus (G') of at least 200 Pa, where the storage modulus of a hydrogel can be measured as described in the Example 1. By way of illustration, some embodiments of the hydrogels have a G' in the range from 1 Pa to 3500 Pa. Moreover, because different functional groups are used for crosslinking and photoexcitation, the photophysics of the system can be readily modulated without compromising reactivity.

Polymer networks and gels having spatially heterogeneous mechanical properties can be formed by irradiating different regions of the networks and gels for different time durations, different radiation intensities, and/or different wavelengths of radiation. In this way, the hydrogels can be designed to mimic various synthetic and naturally occurring materials, such as biological organs which are composed of multiple types of tissue microenvironments having distinct stiffness properties. The stiffness patterns and gradients can be erased and/or modified by one or more additional light patterning steps. This spatial and temporal control of the viscoelastic properties of the networks and gels can be achieved, for example, by irradiating the networks and gels through a photomask or using confocal microscopy. Using these techniques, relatively stiff and relatively soft regions and/or stiffness gradients can be patterned into a gel in the presence of biological cells. The $G'_{max}$ of the relatively stiff and relatively soft regions can differ by a factor of two or more. For example, the two regions can have $G'_{max}$ values that differ by a factor of at least 10, a factor of at least 100, or a factor of at least 1000. In addition, one or more areas of the gel can remain non-irradiated, and these non-irradiated areas will remain in the sol state and be removed by rinsing.

The ability to provide reversible photocontrolled spatially and temporally tunable viscoelastic properties is significant for tissue engineering applications because different cellular microenvironments can present spatiotemporally heterogeneous cues, which can affect spreading, migration, proliferation, organ function, and stem cell differentiation. By tuning the properties of hydrogels used as cell culture substrates, cyclic and complex temporal cues in biology (e.g. ovulation, hormone sensing and release, stem cell differentiation, age-related fibrosis, and tumor metastasis) can be mimicked.

Because hydrogels with spatially and temporally tunable viscoelastic properties can be made using the present methods, the hydrogels can be used for a variety of applications. For example, hydrogels having mechanical properties and water contents that approximate those of living biological tissues can be used as cell culturing scaffolds for tissue engineering applications, provided the polymers are bio- and cytocompatible. By way of illustration, gels having G' values in the range from 0.1 to 1 kPa can be formed to mimic brain tissue and nervous tissue; gels having G' values in the range from 1 to 10 kPa can be formed to mimic liver, fat, breast gland, relaxed muscle, and tendon tissues; gels having G' values in the range from $10^2$ to $10^3$ kPa can be formed to mimic dermis, contracted muscle, and cartilage tissues; and gels having G' values in the range from $10^5$ to $10^7$ kPa can be formed to mimic bone.

The hydrogels can be used as tissue growth scaffolds by seeding the scaffolds with living biological cells or by photogelation of the compositions that also include the biological cells. Tissue can be grown by culturing the seeded scaffolds in a cell growth culture medium. Human mesenchymal stem cells, hematopoetic stem cells, embryonic stem cells, pluripotent stem cells, osteoblasts, chondrocytes, fibroblasts, endothelial cells, and myocytes are examples of the types of cells with which the scaffolds can be seeded.

Figure 4:
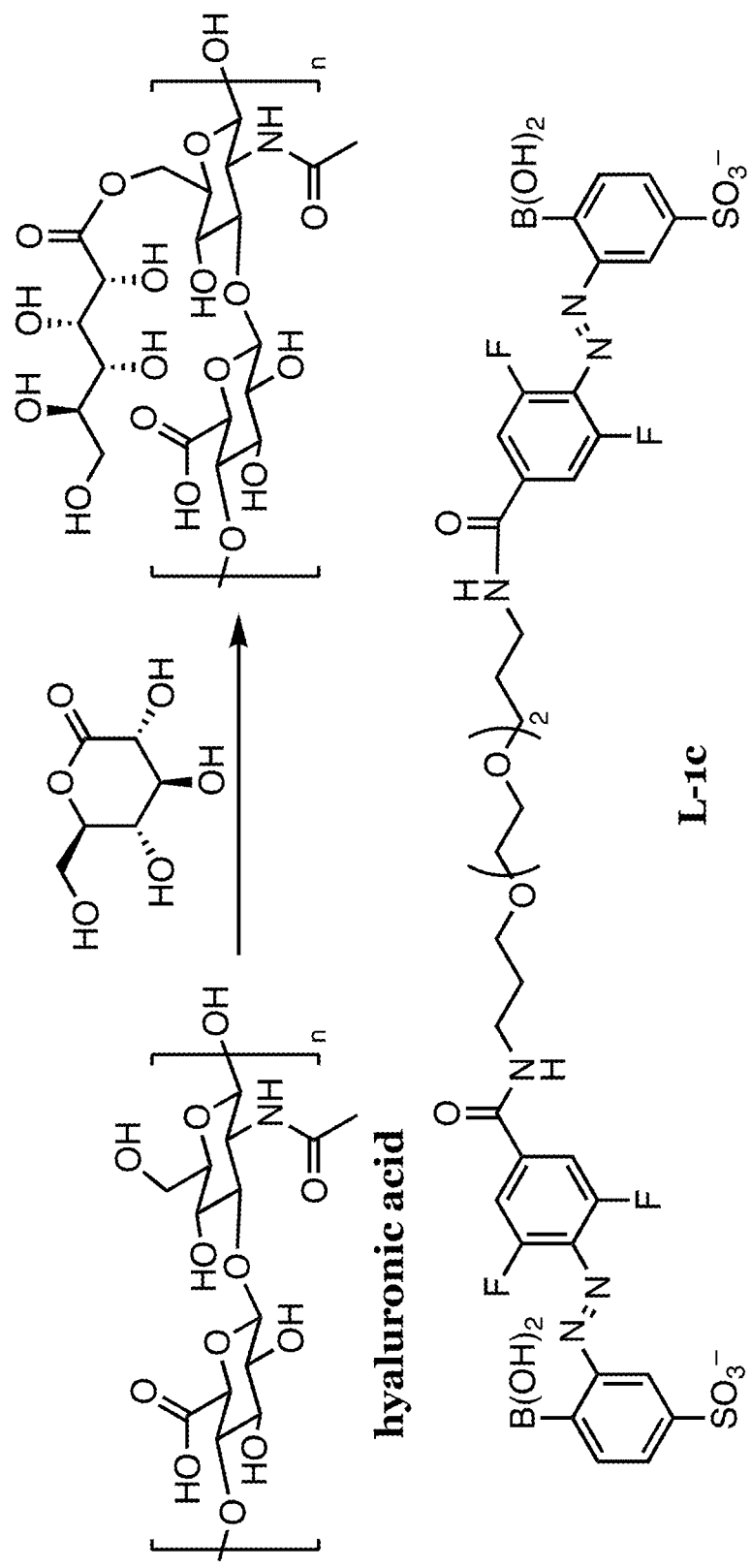
FIG. 4 depicts a diol-modified hyaluronic acid and a telechelic azobenzene boronic acid linker that can be used to make a HA-derived photoresponsive gel.

Modified hyaluronic acid (HA) is an example of a diol group-bearing polymer that can be used to form a hydrogel that mimics ECM. HA is animal derived but available as reproducible, highly purified (growth-factor-free) samples in a variety of molecular weights. HA is a structural component in ECM and regulator of cell behavior, and is used as the key polymeric component for many semi-synthetic biomaterials. HA can be modified with diol end groups by grafting HA with δ-gluconolactone (FIG. 4, top panel). An HA-based gel can then be formed by photocrosslinking the modified HA with a water-soluble, bis-azobenzene boronic acid linker, such as L-1c (FIG. 4, bottom panel). By way of illustration only, HA polymers having molecular weights in the range from 5 kDa to 5000 kDa can be used.

In other embodiments of an ECM mimicking material, a reversibly photocrosslinkable gel is combined with a fiber-forming biomaterial, such as collagen, fibronectin, or ECM itself to create materials that preserve the fibrillar architecture of ECM, while enabling spatiotemporal control. The fiber-forming biomaterials are able to form fibrillar supramolecular aggregates. These materials, which comprise interpenetrating networks of a fiber-forming biomaterial (e.g., decellularized ECM or fiber-forming ECM components) and a synthetic hydrogel of a type described herein as different phases, combine the advantages of photocontrol with the biochemical signals and fibrous morphology of ECM. This fibrillar architecture is important for cell adhesion and migration. The interpenetrating networks have tunable mechanics attributable to the reversible crosslinking properties of the polymers in the gel. The ratios of diol end group-bearing polymers, azobenzene boronic acid crosslinker, and fiber-forming components can be adjusted to tailor the mechanical properties and photoresponse of the materials. The interpenetrating networks can be prepared by pre-mixing the diol end group-bearing polymers, azobenzene boronic acid crosslinker, and fiber-forming components and incubating the resulting composite at, for example, 37° C. Alternatively, the film-forming component can be molded at, for example, 37° C. and then combined with a solution of the gel-forming components.

An example of an interpenetrating network formed from collagen and a reversibly photocrosslinkable diol-functionalized PEG polymer is described in Example 3. An interpenetrating network of collagen and other polymers, such as a diol-functionalized HA polymer, could also be synthesized. An example of an interpenetrating network formed from decellularized ECM and a reversibly crosslinkable diol-functionalized PEG polymer is described in Example 4. An interpenetrating network of decellularized ECM and other polymers, such as a diol-functionalized HA polymer, could also be synthesized. The interpenetrating networks can be used for a variety of applications.

As cell culturing materials and growth scaffolds, the gels and interpenetrating networks can be used to study and control a variety of cell behaviors as a function of substrate stiffness and/or stress relaxation. For example, the gels and interpenetrating networks can be used to study or control cell spreading as a function of stiffness for cells that are seeded on or encapsulated within the gels and interpenetrating networks. The gels and interpenetrating networks can also be used to study or control the effects of temporally changing stiffness (soft to stiff or vice versa) on cell fate. For the synthetic ECM-based gels and interpenetrating networks, such studies have relevance to developmental and disease processes, which are characterized by increasingly stiff tissues.

EXAMPLES

Example 1: Poly(ethylene glycol)-Based Hydrogels

In this example, the development of a platform to reversibly tune the mechanical properties of dynamic hydrogels that use photoswitches to control the reactivity of dynamic covalent crosslinks is reported. Small-molecule studies suggest that the conformation of the azobenzene boronic acid determines the equilibrium constant for condensation with diol, with an increase in $K_{eq}$ for the Z isomer. The increase in the equilibrium constant generates a higher crosslink density in the hydrogel network, resulting in stiffening. Because of the dynamic nature of the boronic ester crosslink, these hydrogels are viscoelastic and stress-relaxing, and have stiffness that can be tuned independently of crosslink exchange rates. This approach can be generalized to an o-difluoroazobenzene with superior photophysical properties, enabling mechanical control of the hydrogel solely with visible light.

Figure 5:
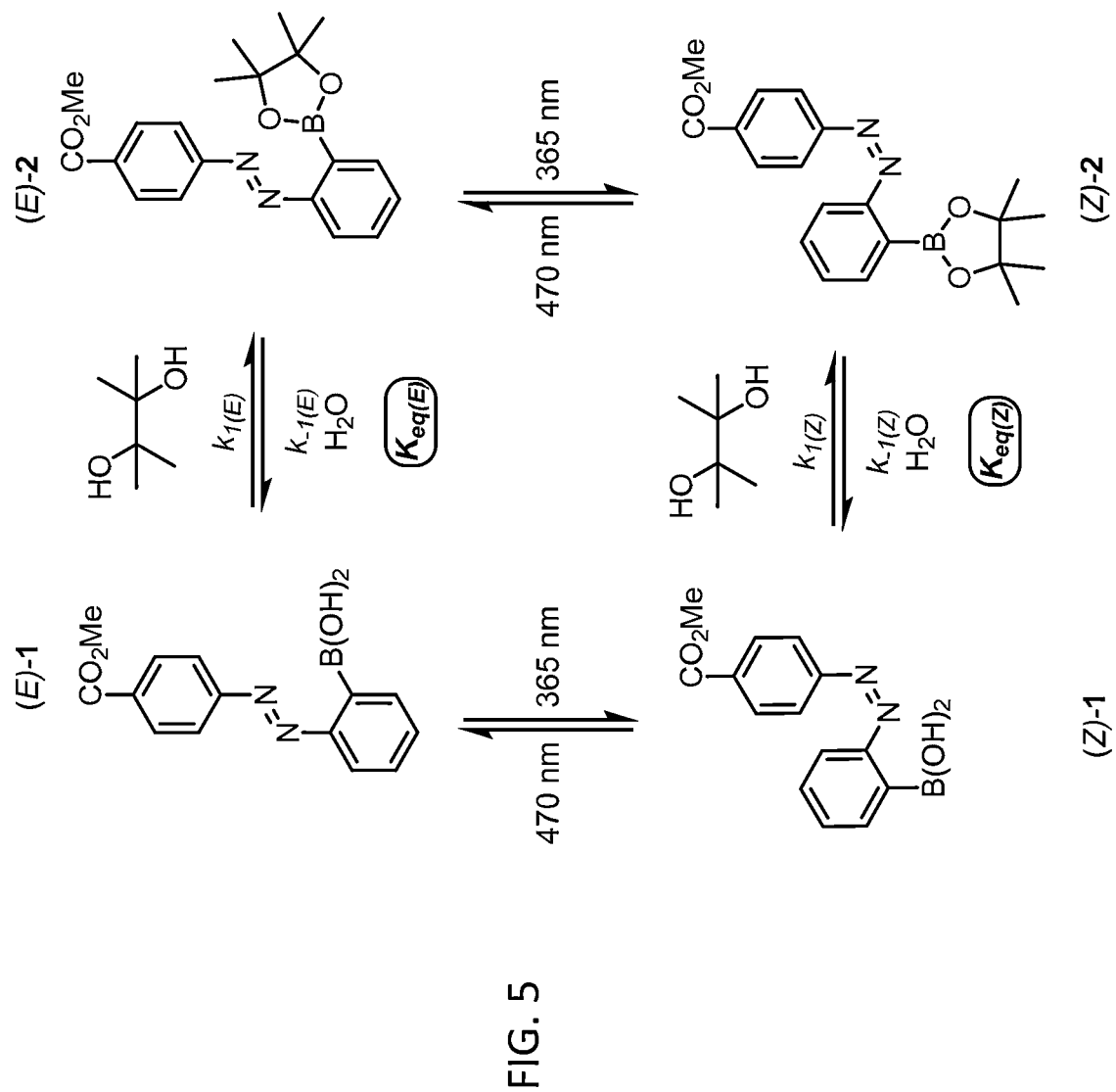
FIG. 5 depicts a small-molecule model system for studying the relative rates and equilibrium constants for reversible esterification of an o-azobenzene boronic acid.

A small-molecule model compound, azobenzene 1, was first designed, in which the boronic acid was positioned ortho to the azo group (FIG. 5). Irradiation of (E)-1 with 365-nm light provided a 88:12 mixture of Z and E isomers. This mixture was subjected to excess pinacol in acetonitrile-water (1:1 v/v, 25° C.) to determine the apparent rates and equilibrium constants of boronic acid (1) esterification and boronic ester (2) hydrolysis for each isomer. While other 1,2- and 1,3-diols were hydrolyzed too quickly to be studied, the unusually slow rate of pinacol hydrolysis allowed the E and Z isomers to be resolved and their reaction kinetics to be monitored by high-performance liquid chromatography (HPLC; see Supporting Information (SI) for details).

Figure 6B:
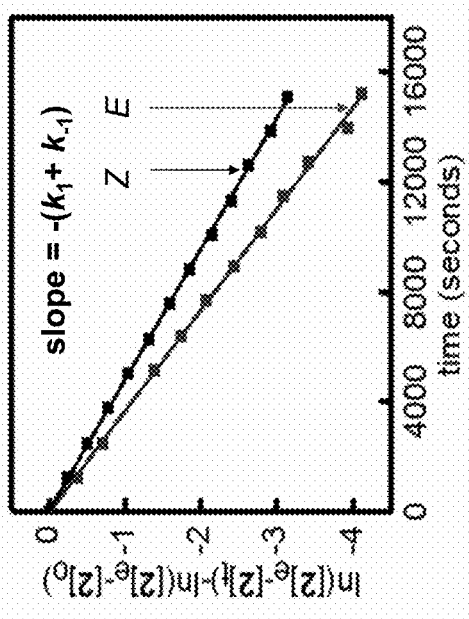
FIG. 6B depicts linear fit of data from FIG. 6A to determine apparent rates of esterification and hydrolysis of E and Z isomers.
Figure 6D:
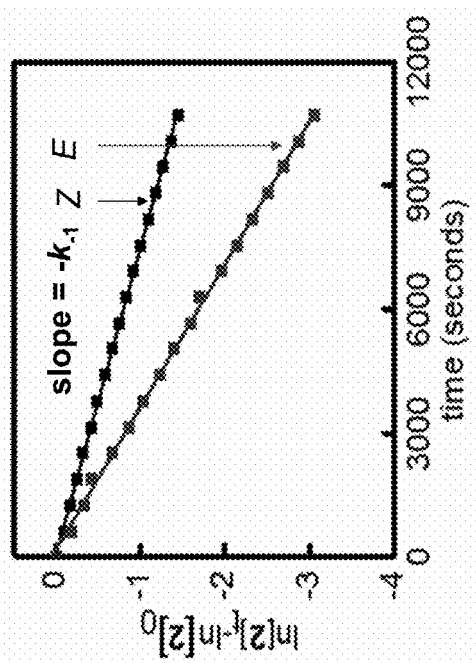
FIG. 6D depicts linear fit of data from FIG. 6C to confirm apparent rates of hydrolysis for E and Z isomers.
Figure 6A:
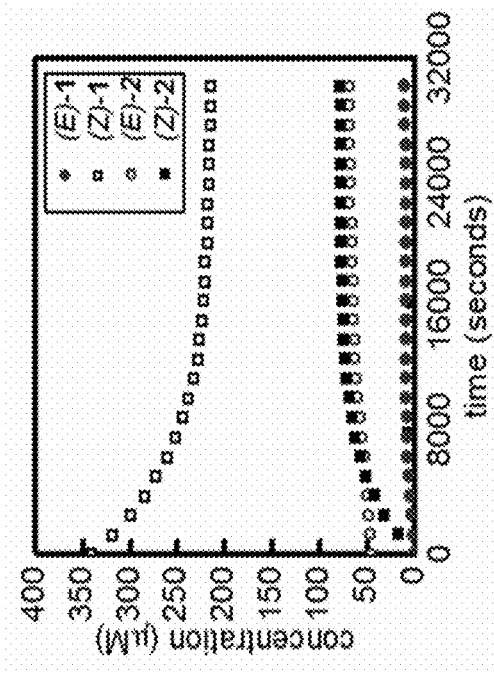
FIG. 6A depicts esterification of 400 µM mixture of (E)- and (Z)-1 with 40 mM of pinacol in 1:1 ACN:$H_2O$.
Figure 6C:
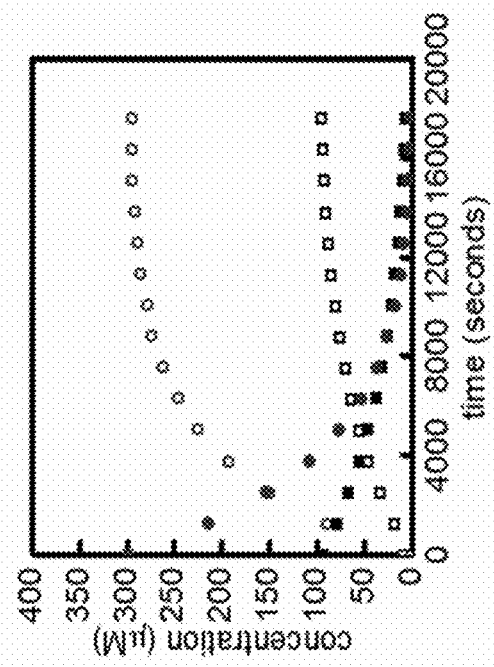
FIG. 6C depicts hydrolysis of 400 M mixture of (E)- and (Z)-2 in 1:1 ACN:$H_2O$.

This initial experiment revealed a difference in the reactivity of (E)-1 and (Z)-1. After 8 hours, the reactions had reached equilibrium, with 39% conversion of (Z)-1 to (Z)-2 and only 9% conversion of (E)-1 to (E)-2 (FIG. 6A). Using a reversible pseudo-first-order kinetic model, it was determined that the esterification of (Z)-1 was 2.1 times faster than the esterification of (E)-1 ($k_1$) (FIG. 6B, Table 1). The rates of hydrolysis could also be extracted from this model: (E)-2 underwent hydrolysis 2.0 times faster than (Z)-2 did ($k_{-1}$). These apparent rate constants for hydrolysis were verified by hydrolyzing a mixture of (E)-2 and (Z)-2 under irreversible pseudo-first-order conditions (FIGS. 6C and 6D). Taken together, the apparent equilibrium to form boronic ester from boronic acid and pinacol is 4.3 times more favorable for the Z isomer relative to the E isomer. While convenient for small-molecule kinetic studies, the rate of pinacol ester formation is too slow to be practical for gelation. Thus, a less sterically hindered diol was used for hydrogel studies.

Figure 8:
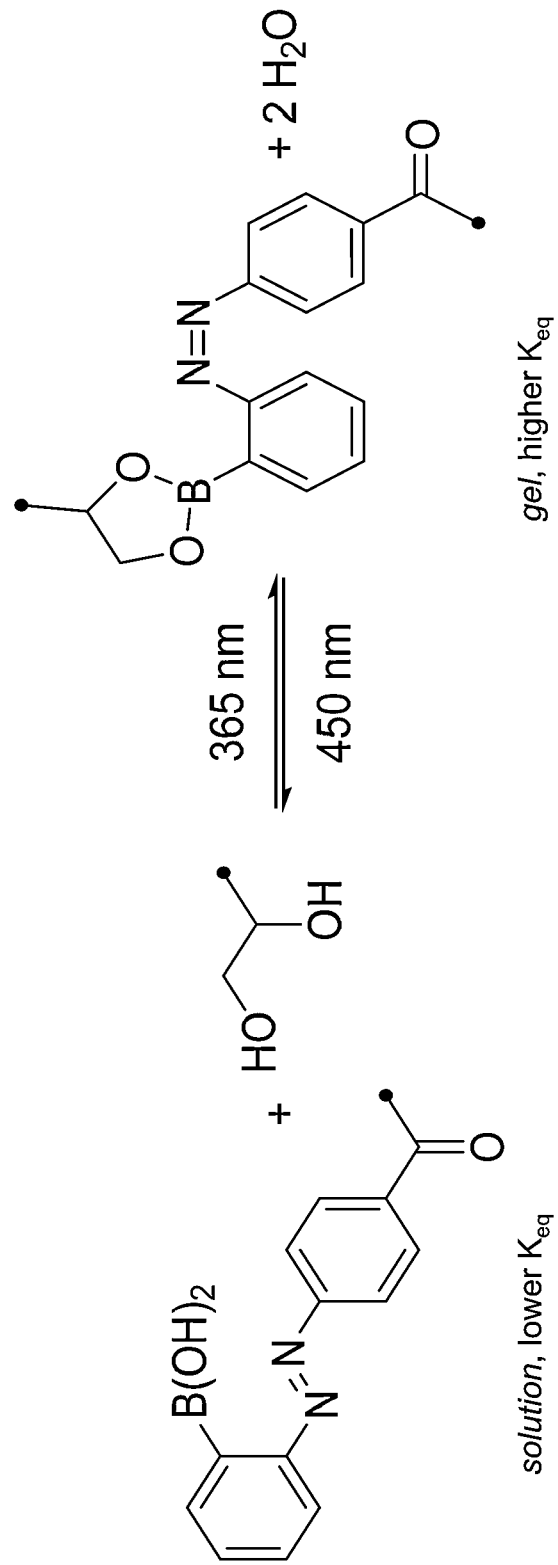
FIG. 8 shows the reversible sol-gel transition of a mixture of P1 and P2 (1:1, 10 w/v % in PBS, pH 7.5).

%). Prior to irradiation, the mixture was a sol, according to the flow-inversion method. Irradiation with a 365 nm flashlight for 10 minutes induced partial E to Z isomerization of the azobenzene photoswitch and led to gelation. Irradiating this gel for 30 seconds with blue LEDs (470 nm) caused Z to E isomerization and returned the mixture to the sol state. The sol-gel cycles could be repeated multiple times by sequential irradiation with 365 and 470 nm light (FIG. 8).

In contrast, P1 and control polymer P3 (a para-boronic acid) formed a gel without irradiation, and this gel was not photoresponsive. This observation indicates that proximity to the azo group, rather than an inductive/resonance or rigidity effect, was responsible for the photoresponse. The combination of P1 and P4, lacking a boronic acid, formed a sol regardless of irradiation, providing evidence that the boronic ester was the crosslink. (See SI for rheological characterization of the control gels.)

Figure 9A:
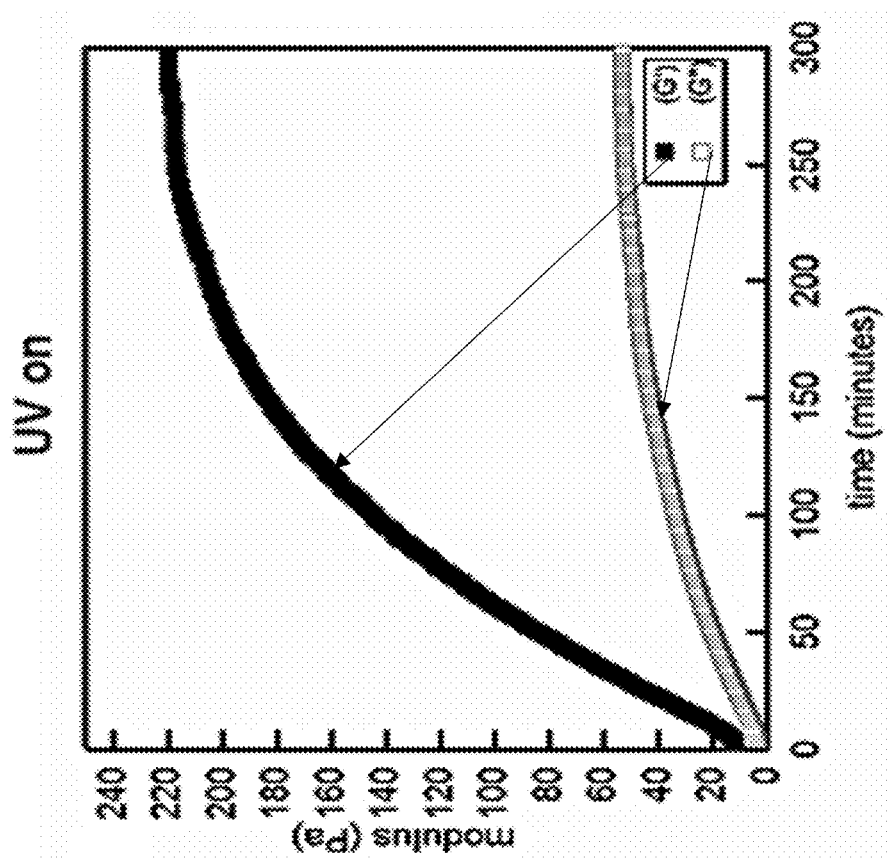
FIGS. 9A-9C depict the representative photorheological characterization of the hydrogels of Example 1.
Figure 9B:
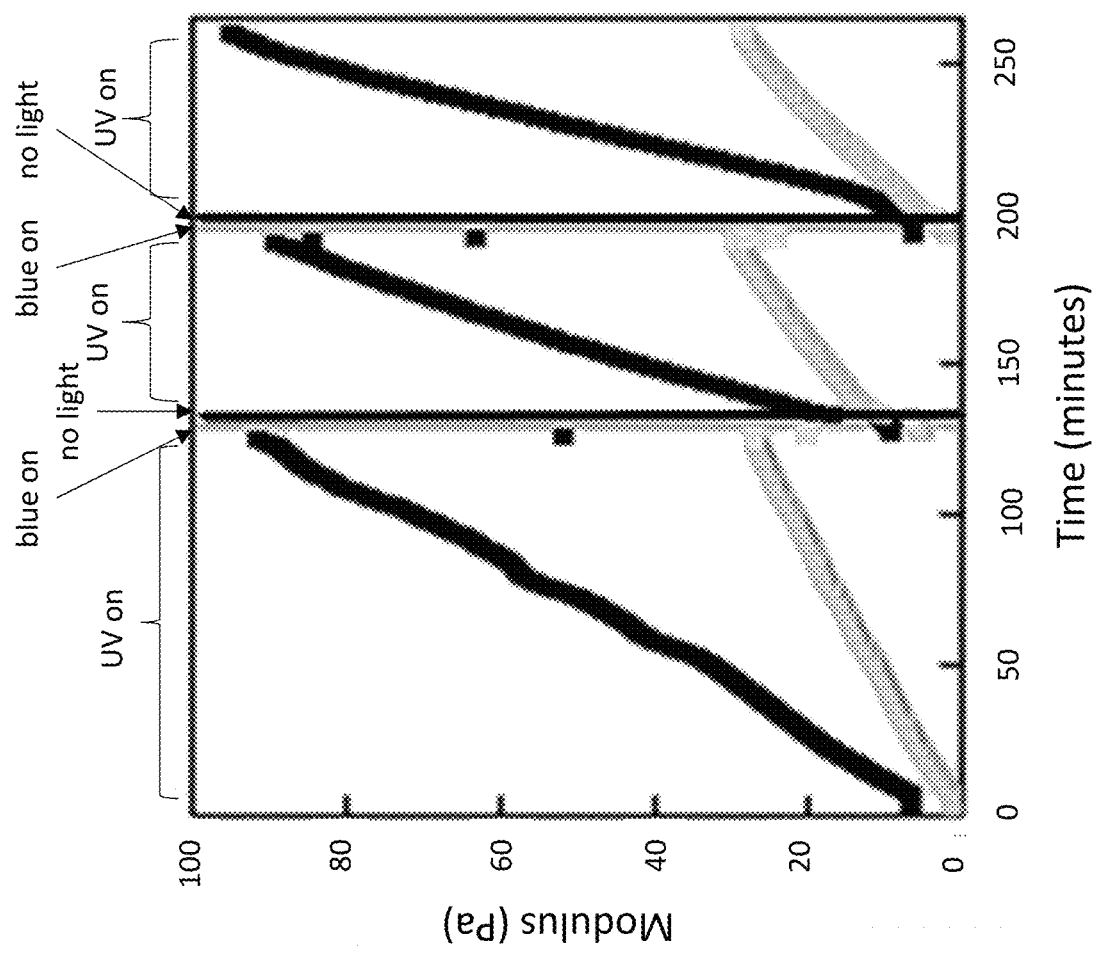

To quantitatively assess the photoresponsive bulk mechanical properties of the hydrogel, photo-oscillatory rheology was performed at constant strain and frequency within the linear viscoelastic regime. Upon constant irradiation of mixtures of P1 and P2 (1:1, 10 w/v % in PBS, pH 7.5) with 365-nm LED light, the storage (G') and loss moduli (G"), which represent the elastic and viscous characteristics of the hydrogel, respectively, increased by over an order of magnitude. The maximum storage modulus (220 Pa) was achieved after approximately 3 hours of irradiation (FIG. 9A). Importantly, it could be quantitatively demonstrated that this change in mechanical properties was reversible by performing photorheology with alternating 365- and 470-nm light (FIG. 9B). After stiffening the gel with 365-nm light for 2 hours, irradiation with 470-nm light for 2 minutes returned the network to its original state. Gelation could be repeated by irradiation with 365-nm light. In contrast to strategies

TABLE 1

Apparent rate and equilibrium constants for the small-molecule model study. Data are the average of three experiments.

| Configuration | $K_{eq}$ [a] | $k_1$ (s$^{-1}$) [a] | $k_{-1}$ (s$^{-1}$) [a] | $k_{-1}$ (s$^{-1}$) [b] |
|---|---|---|---|---|
| E | 0.090 ± 0.016 | 2.56 ± 0.28 × 10$^{-5}$ | 2.76 ± 0.32 × 10$^{-4}$ | 2.83 ± 0.06 × 10$^{-4}$ |
| Z | 0.39 ± 0.024 | 5.39 ± 0.45 × 10$^{-5}$ | 1.39 ± 0.20 × 10$^{-4}$ | 1.45 ± 0.10 × 10$^{-4}$ |
| Z/E | 4.3 | 2.11 | 0.504 | 0.512 |

[a] Apparent equilibrium constants and rate constants obtained from the reversible esterification experiment.
[b] Apparent rate constants obtained from the irreversible hydrolysis experiments.

Hydrogel Synthesis and Rheological Characterization

Figure 7:
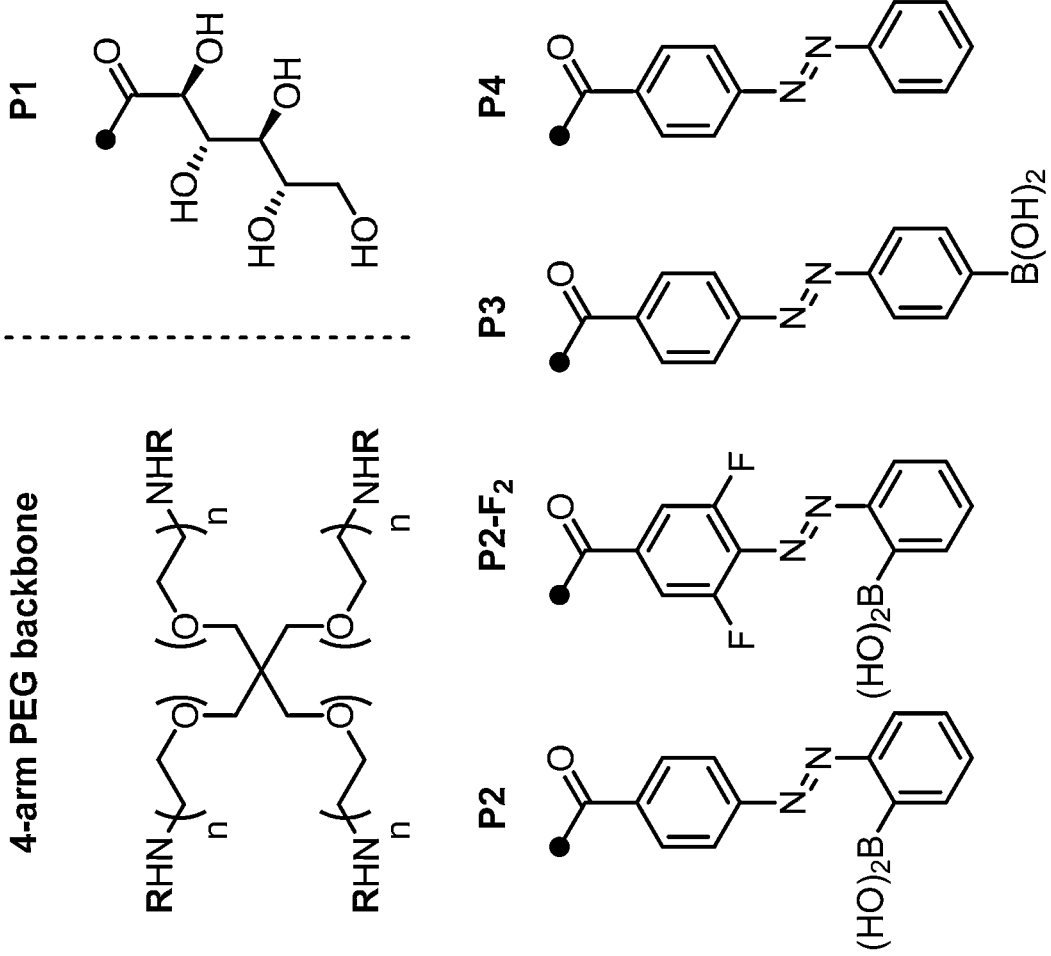
FIG. 7 depicts the structure of azobenzene- and diol-terminated poly(ethylene glycol) polymers P1-P4.

With these small-molecule data in hand, the next step was to translate the molecular design to photoswitchable networks. A pair of branched polymers, P1 and P2, was prepared with complementary diol and boronic acid functionalities (FIG. 7). The diol-terminated polymer (P1) was synthesized by ring opening glucono-δ-lactone with amine-terminated 4-arm poly(ethylene glycol) (PEG, Mw=5 kDa) according to a literature procedure. (See, Yesilyurt et al., Adv. Mater. 2017, 29; and Yesilyurt, et al., Adv. Mater. 2016, 28, 86.) The boronic acid polymer (P2) was synthesized by coupling the same PEG with the carboxylic acid derivative of compound 1 using carbodiimide coupling chemistry (see SI for details). Control polymers P3 and P4 were synthesized in analogy to P2 to evaluate the role of the ortho-boronic acid.

To qualitatively investigate the effect of irradiation on the boronic ester hydrogel, P1 and P2 were mixed in a 1:1 ratio of 0.1 M phosphate-buffered saline (PBS) at pH 7.5 (10 w/v based on photocleavage or photoinitiated polymerization, water was the only byproduct and required an exogenous reagent.

Interestingly, this system stiffened in the Z conformation and softened in the E conformation. While the measured rate and equilibrium constants cannot be directly correlated for the small-molecule model system (Table 1) to the viscoelastic behavior of the P1/P2 hydrogel due to the change in diol, it is believed that the Z azobenzene boronic acid experienced more favorable equilibrium towards the boronic ester compared to the E isomer. Since the boronic ester was the elastically effective crosslink, a higher equilibrium corresponded to higher crosslink density and thus a stiffer gel.

The viscoelastic properties of the hydrogel system were next characterized as a function of irradiation. Networks formed from irreversible covalent bonds are elastic, and exhibit frequency independent moduli because the crosslinks are fixed. Dynamically crosslinked networks have time-dependent properties. At fast time scales, the oscillation occurs faster than bonds can rearrange, thus the networks behave as gels. At slow time scales, crosslinks can exchange faster than the oscillation, and the networks behave as liquids. The crossover frequency ($\omega_c$) at which G' and G" are equal corresponds to the oscillation frequency at which the viscoelastic material transitions from solid to liquid.

Figure 9C:
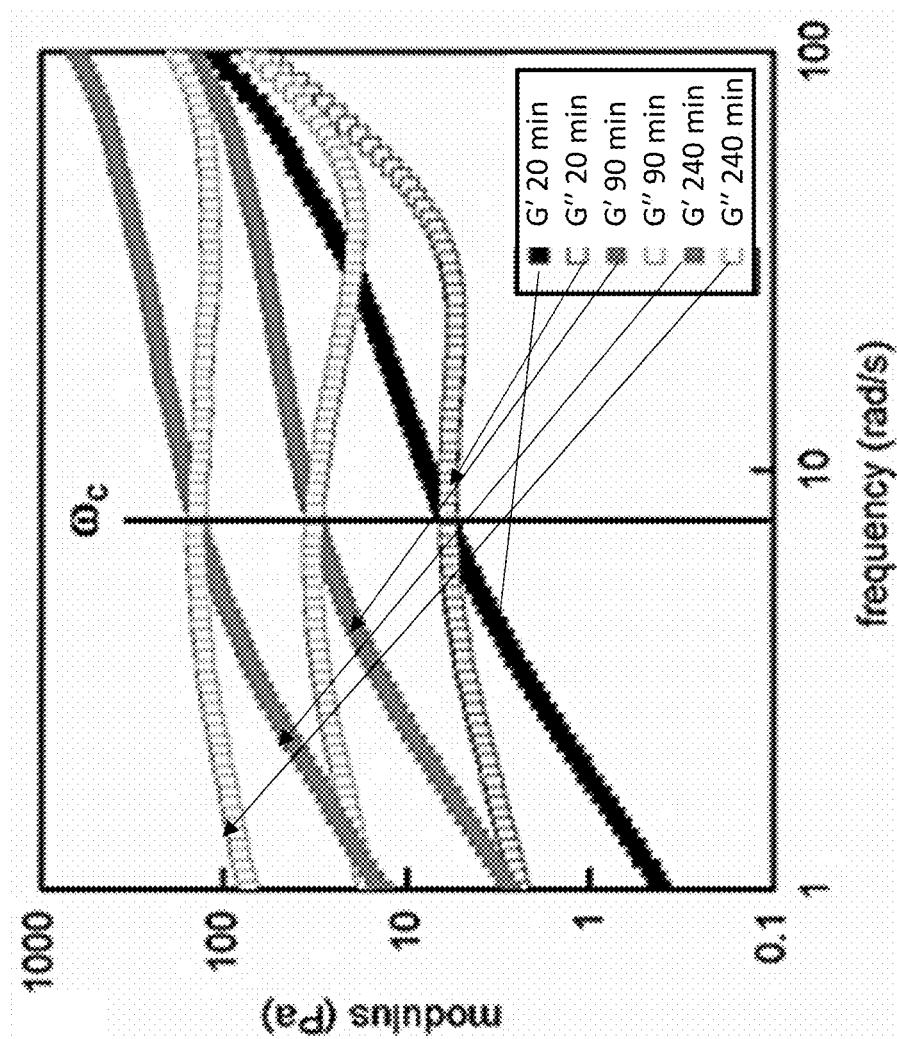
Figures 12, 13:
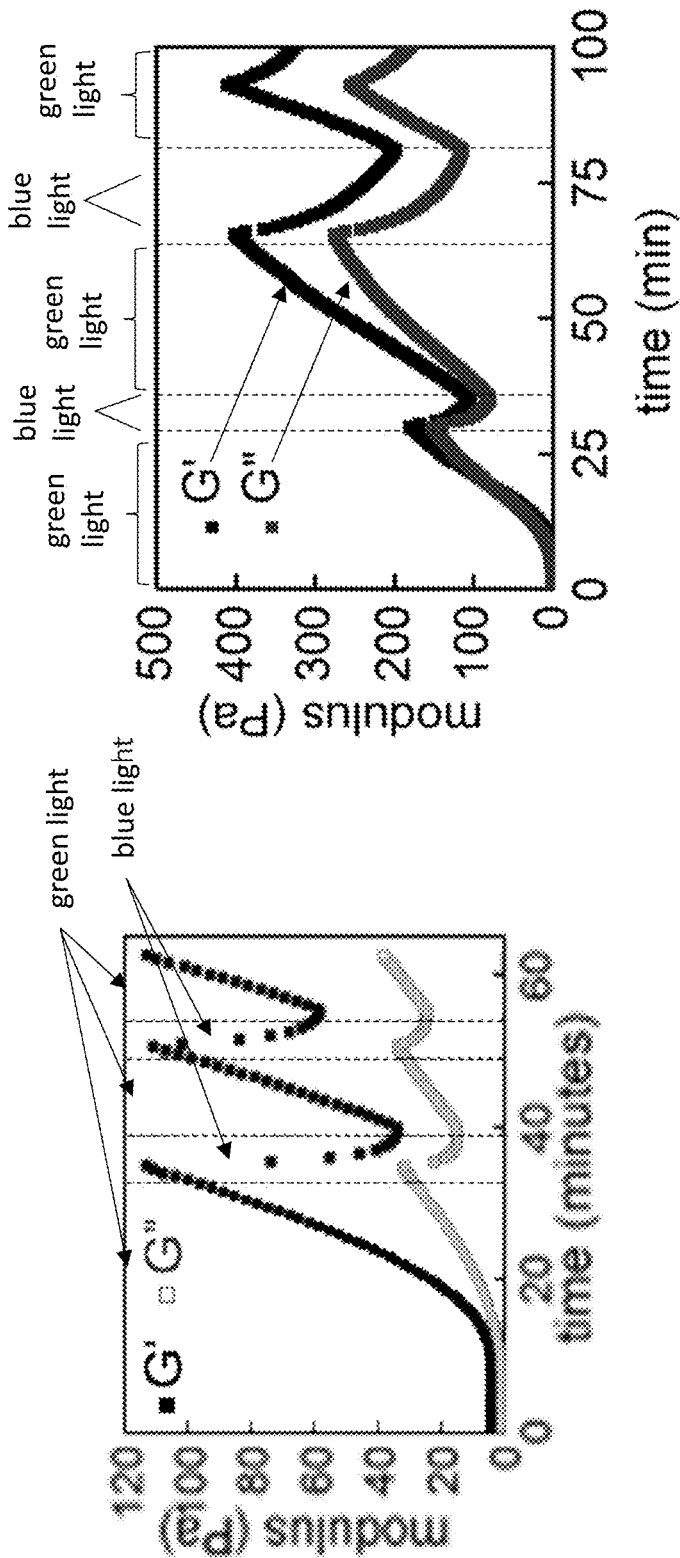
FIG. 12 depicts the photoresponse of hybrid P1/P2-$F_2$/collagen interpenetrating network.
FIG. 13 depicts preliminary data for a gel/liver extracellular matrix (ECM) hybrid interpenetrating network with oscillatory shear rheology.

Frequency sweeps were performed on mixtures of P1 and P2 (1:1, 10 w/v % in PBS, pH 7.5), and frequency-dependent viscoelastic behavior was observed. Consistent with measurements at constant frequency, when these measurements were performed after various intervals of UV irradiation (20-240 minutes, FIG. 9C), both storage and loss moduli increased. Interestingly, the crossover frequency at 7 rad/s was nearly independent of irradiation time. Consistent with these oscillatory data, the gels relaxed strain-induced stress on the order of seconds (see SI).

The crossover frequency of a dynamic frequency sweep measurement is often correlated to the molecular processes underlying crosslink exchange. In this case, the stress-relaxing process was assigned to be hydrolysis of the boronic ester. The rheological data demonstrated that through photocontrolled dynamic covalent crosslinks, an external stimulus could reversibly alter the spatial structure of a viscoelastic network (crosslink density) without significantly altering the temporal hierarchy (relaxation modes). Therefore, it is presumed that for this particular boronic acid/diol combination, the change in equilibrium constants for E versus Z azobenzene boronic acid, rather than changes in hydrolysis rates, underlay the phototunable change in stiffness. Strategic modifications of the boronic acid and diol structures could additionally enable turning of relaxation modes.

Visible-Light Photoswitching

Next, the system was optimized such that photoreversible viscoelasticity could be achieved with visible light. In addition to lower reactivity, visible light offers enhanced hydrogel penetration. Polymer P2-$F_2$ (FIG. 7) was synthesized. Hydrogels prepared from mixtures of P1 and P2-$F_2$ at (1:1, 10 w/v % in PBS, pH 7.5) demonstrated reversible sol to gel transitions by alternative irradiation with green (530 nm) and blue (470 nm) LEDs. Rheological characterization confirmed that the stiffness of the gels could be reversibly controlled, and the hydrogels were viscoelastic (FIG. 10A). Importantly, gels synthesized from P2-$F_2$ exhibited moduli that were over two factors larger than those formed from P2, which may be due to a higher binding affinity of the fluorinated azobenzene boronic acid with diols. Notably, while G' increased as a function of irradiation time, the stress relation rate of the gel did not change (FIG. 10B). Thus, this viscoelastic hydrogel demonstrated stiffness tunability independent of stress relaxation.

Gratifyingly, the P1/P2-$F_2$ gel (10 w/v % in PBS, pH 7.5) was sufficiently stiff to form freestanding shapes, so the robustness of the gel could be evaluated. Once cut, these hydrogels were able to heal in minutes at room temperature, which was attributed to the dynamic exchange between boronic acids and diols. The gels formed from 1 hour of irradiation with green light and the thermal half-life of the Z conformation was at least one month; the stiffness being maintained by excluding blue light from the room's fluorescent lights with filters. Attempts to swell the gels in solutions of PBS were consistent with a lightly crosslinked dynamic network: the material was fully dissolved after 6 hours at 23° C. The long-term utility of these hydrogels can be further improved by increasing branch functionality and tuning the identity of the diol end-groups to increase $K_{eq}$.

Cytocompatibility of the gels. To evaluate the cytocompatibility of the P1/P2-$F_2$ gels, which can be tuned solely with visible light, HeLa cells were encapsulated in P1/P2-$F_2$ (10 wt % Dulbecco's Modified Eagle Medium (DMEM) with 10% fetal bovine serum (FBS)), which formed a soft gel. As a control, the cytotoxic compound auranofin (20 μM) was introduced into the gels with encapsulated cells. After 24 hours, the viability of the encapsulated cells was quantified using a rezasurin reduction assay with a fluorescence plate reader. (Uzarski, J. S. et al., *Biomaterials* 2017, 129, 163-175.) Cells encapsulated in the gels maintained >80% viability relative to cells in FBS-modified DMEM cultured on standard plastic substrates, while <10% of the control cells exposed to the cytotoxic compound survived.

Supporting Information

General Information

General procedures. Unless otherwise noted, reactions were performed under Ar atmosphere in oven-dried (120° C.) glassware. Reaction progress was monitored by thin layer chromatography (Merk silica gel 60 $F_{254}$ plates), and visualizing was performed with fluorescence quenching, $KMnO_4$, or ninhydrin stains. Automated column chromatography was performed using SiliCycle SiliaFlash F60 (40-63 μm, 60 Å) in SNAP cartridges on a Biotage Isolera One. Organic solvents were removed in vacuo using a rotary evaporator (Büchi Rotovapor R-100, ~20-200 torr), and residual solvent was removed under high vacuum (<100 mtorr). Water-soluble polymers were purified by dialysis using SnakeSkin Dialysis Tubing (3.5 kDa cutoff, 16 mm diameter) purchased from Fisher.

Materials. Commercial reagents were purchased from Sigma-Aldrich, Acros, Alfa Aesar, TCI, or Oakwood and used as received. 4-Arm PEG-$NH_2$ HCl salt ($M_w$, 5 kDa) was purchased from JenKem, and was azeotroped with toluene (3×) and melted under high vacuum (<100 mtorr) prior to functionalization.

Instrumentation. Proton nuclear magnetic resonance ($^1H$ NMR) spectra and carbon nuclear magnetic resonance ($^{13}C$ NMR) spectra were recorded on Bruker AVANCE-500 spectrometers at 500 MHz and 125 MHz, and referenced to the solvent residual peaks. Boron nuclear magnetic resonance ($^{11}B$ NMR) spectra were recorded on Bruker AVANCE-400 spectrometers at 128 MHz. $BF_3 \cdot OEt_2$ in $CDCl_3$ in a capillary was used as a reference for $^{11}B$ NMR (0 ppm) in Wilmad Precision NMR tubes (CFQ, 500 MHz, OD: 5 mm, wall thickness: 0.38 mm). NMR data are represented as follows: chemical shift (δ ppm), multiplicity (s=singlet, d=doublet, t=triplet, q=quartet, m=multiplet), coupling constant in Hertz (Hz), integration. UV-vis spectra were collected on a Cary 5000 UV-vis-NIR spectrophotometer with an Hg lamp; cuvettes were 10-mm path length quartz cells (Starna 23-Q-10). Liquid chromatography-mass spectrometry (LCMS) kinetics experiments were performed on a liquid chromatography-mass spectrometry system (Agilent 6120 Quadrupole LC/MS) equipped with a variable-wavelength detector. Infrared spectroscopy was performed on a Thermo Nicolet iS10 with a ZnSe crystal ATR attachment. Size exclusion chromatography (SEC) measurements were performed in stabilized, HPLC-grade tetrahydrofuran using an Agilent 1260 Infinity II system with variable-wavelength diode array (254, 450, and 530 nm) and refractive index detectors, guard column (Agilent PLgel; 5 μm; 50×7.5 mm), and three analytical columns (Agilent PLgel; 5 μm; 300×7.5 mm; $10^5$, $10^4$, and $10^3$ Å pore sizes). The instrument was calibrated with narrow-dispersity polystyrene standards between 640 Da and 2300 kDa (Polymer Standards Service GmbH). All runs were performed at 1.0 mL/min flow rate and 40° C. Molecular weight values were calculated based on the refractive index signal.

Synthesis of Azobenzene Boronic Acids

Figure 14:
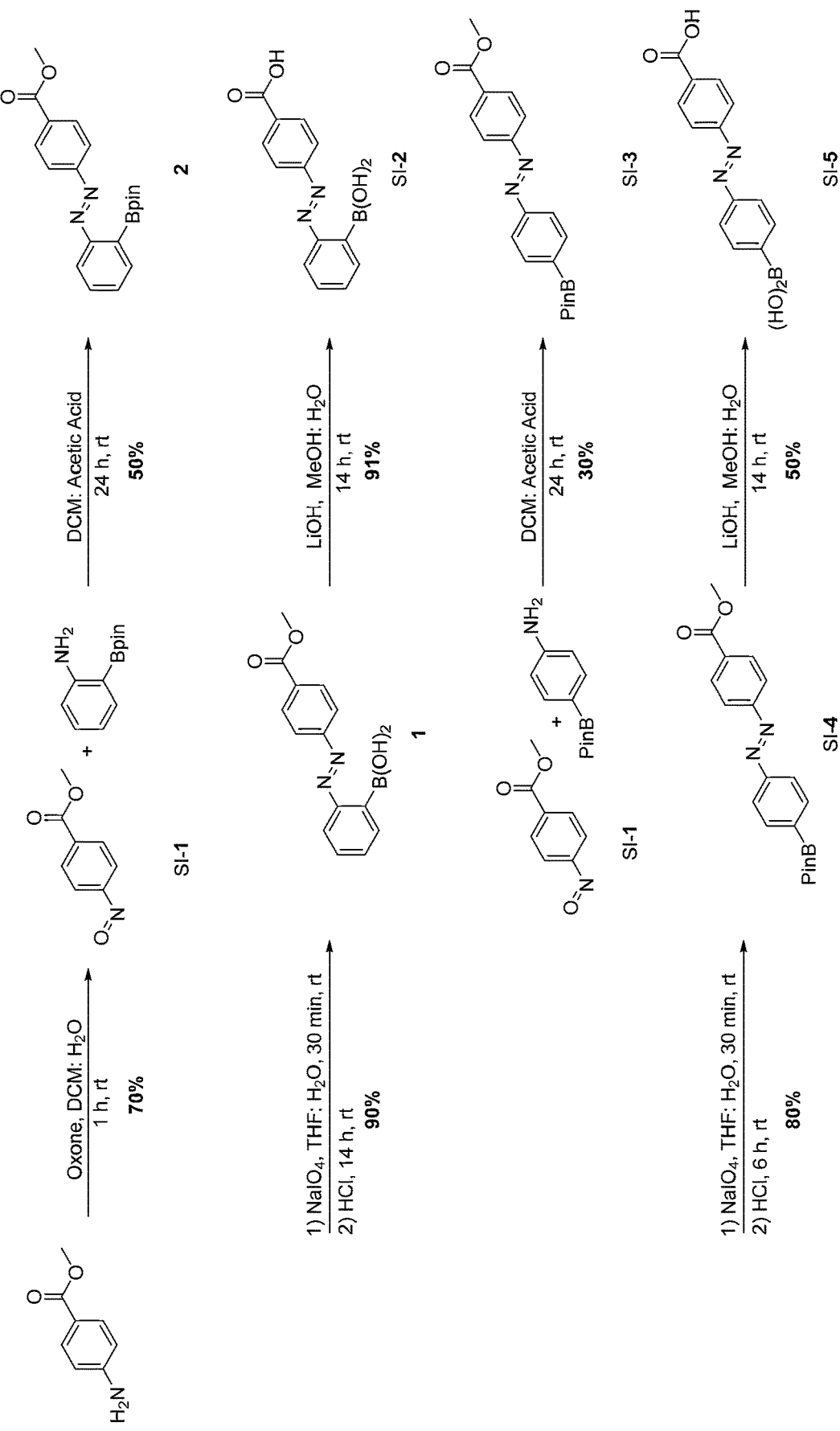
FIG. 14 shows a synthetic route of small molecules 1 and 2 for kinetic studies and compound SI-2 and SI-5 for synthesis of control polymers P2 and P3 in Example 1.

The synthetic route of small molecules 1 and 2 for kinetic studies and compound SI-2 and SI-5 for synthesis of control polymers P2 and P3 is shown in Scheme S1 in FIG. 14.

Methyl 4-nitrosobenzoate (SI-1)

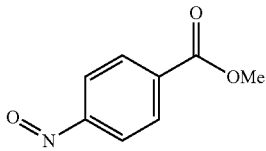 [SMILES: COC(=O)c1ccc(N=O)cc1]

Based on a modified from literature procedure, methyl 4-aminobenzoate (3 g, 20 mmol) was dissolved in 66 mL of dichloromethane (DCM) into a 500-mL round-bottomed flask (RBF) equipped with stir bar. (Priewisch, B. et al., *The Journal of Organic Chemistry*. 2005, 70, 2350.) Oxone (20 g, 40 mmol) was dissolved into 250 mL of deionized water and then added to the reaction mixture (capped with rubber septum which was pierced with a needle, exposed to air), and the reaction was aged for 1 hour with high stirring. Over the course of the reaction, the biphasic solution developed into an intense neon green color. The product was extracted against water (1×), 1M HCl (2×), and 1M NaOH (3×). The organic layer was dried over sodium sulfate and concentrated in vacuo to give methyl 4-nitrosobenzoate (2.26 g, 70%). This product was used in the subsequent step without further purification. $^1$H NMR (500 MHz, Chloroform-d) δ 8.30 (d, J=8.5 Hz, 2H), 7.94 (d, J=8.5 Hz, 2H), 3.98 (s, 3H).

Methyl (E)-4-((2-(4,4,5,5-tetramethyl-1,3,2,-dioxaborolan-2-yl)phenyl)diazinyl)benzoate (2)

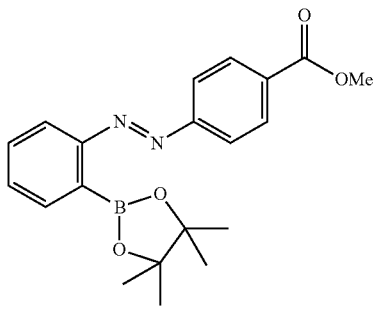 [SMILES: COC(=O)c1ccc(/N=N/c2ccccc2B2OC(C)(C)C(C)(C)O2)cc1]

SI-1 (4.4 g, 27 mmol) and 2-(4,4,5,5,-tetramethyl-1,3,2-dioxaborolan-2-yl)aniline (6.1 g, 28 mmol) were dissolved in 100 mL of DCM into a 250 mL RBF, to which 20 mL of acetic acid was added. The reaction was stirred for 24 hours, open to air. The solution turned black after several hours. Upon consumption of the starting material, the organic layer was washed with 1M HCl (3×), and the organic layer was collected, dried with sodium sulfate, and concentrated in vacuo. Residual acetic acid was removed under high vacuum. The collected solids were diluted in hexane (300 mL), and the precipitate which formed (byproduct) was removed with a glass frit. The red filtrate was concentrated in vacuo to approximately 100 mL and then filtered again. The collected filtrate was concentrated in vacuo to yield an orange solid (~6 g) which was recrystallized from hexane (30 mL) twice to provide the product as a red crystalline solid (5 g, 50%). $^1$H NMR (500 MHz, CDCl$_3$) δ 8.19 (d, J=8.7 Hz, 2H), 7.94 (d, J=8.6 Hz, 2H), 7.81 (d, J=8.0, 1.1 Hz, 1H), 7.75 (d, J=1.5 Hz, 1H), 7.56-7.52 (m, 1H), 7.50-7.46 (m, 1H), 3.96 (s, 3H), 1.36 (s, 12H). $^{13}$C NMR (125 MHz, CDCl$_3$) δ 166.6, 156.9, 155.4, 134.5, 131.5, 130.8, 130.6, 130.5, 122.8, 119.7, 84.0, 52.3, 25.0. $^{11}$B NMR (128 MHz, CDCl$_3$) 31.3. IR (cm$^{-1}$) 2977, 2953, 2925, 2851, 1721, 1597. HRMS m/z expected for C$_{20}$H$_{24}$BN$_2$O$_4$ [M+H]$^+$ 367.18, measured 367.18.

(E)-(2-((4-(methoxycarbonyl)phenyl)diazinyl)phenyl)boronic acid (1)

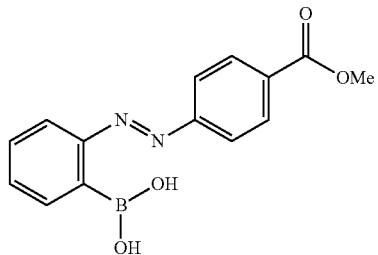 [SMILES: COC(=O)c1ccc(/N=N/c2ccccc2B(O)O)cc1]

2 (5 g, 10 mmol) was dissolved into a 500 mL RBF equipped with a stir bar (capped with a rubber septum which was pierced with a needle, exposed to air). The starting material was dissolved in tetrahydrofuran (THF) (250 mL), providing a clear, deep red solution. Sodium periodate (9 g, 40 mmol) was dissolved in deionized (DI) water (62 mL) and transferred to the solution. After stirring for 30 minutes, 1M HCl (8 mL) was added. The reaction was stirred overnight at room temperature. In the morning, the solution was red and cloudy with precipitate. The THF was removed in vacuo to concentrate the product in water. The resulting suspension was diluted with additional water and filtered to provide an orange/peach-colored solid. The solids were washed with acetonitrile (100 mL) and collected and dried on a glass filter to give the 1 (3.5 g, 90%) as a peach-colored solid. This product was used in the subsequent step without further purification. $^1$H NMR (500 MHz, DMSO-d$_6$) δ 8.19 (d, J=8.4 Hz, 2H), 7.96 (d, J=8.4 Hz, 2H), 7.92 (d, J 6.3 Hz, 1H), 7.83 (s, 2H), 7.59-7.53 (m, 3H), 3.91 (s, 3H). $^{13}$C NMR (126 MHz, DMSO-d$_6$) δ 166.1, 155.0, 154.1, 133.1, 131.9, 131.8, 131.0, 129.6, 123.6, 123.0, 52.9. $^{11}$B NMR (128 MHz, DMSO-d$_6$) 28.4. IR (cm$^{-1}$) 3347 (br), 3198 (br), 3033, 2962, 1723, 1597. LRMS m/z expected for C$_{14}$H$_{14}$BN$_2$O$_4$ [M+H]$^+$ 285.10, measured 285.1.

(E)-4-((2-boronophenyl)diazenyl)benzoic acid (SI-2)

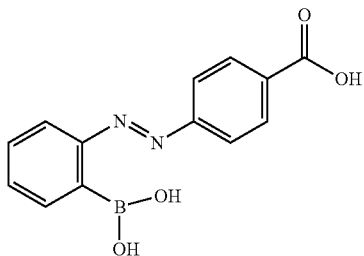 [SMILES: O=C(O)c1ccc(/N=N/c2ccccc2B(O)O)cc1]

1 (3 g, 10 mmol) was dissolved in MeOH (282 mL) in a 1-L RBF equipped with a stir bar, providing a bright red solution. Lithium hydroxide (1 g, 40 mmol) was dissolved into water (58 mL) and transferred to the reaction mixture, which was stirred open to air overnight. The methanol was removed in vacuo, providing a red alkaline aqueous solution. This solution was neutralized with 1M HCl to precipitate the desired product, which was collected on a glass filter and dried in a vacuum oven (100° C.) for 1 hr to provide the title product (2.45 g, 91%) as a peach-colored solid. This product was used in the subsequent step without further purification. $^1$H NMR (500 MHz, DMSO-$d_6$) δ 13.25 (s, 1H), 8.17 (m, 2H), 7.98-7.90 (m, 3H), 7.82 (s, 2H), 7.62-7.52 (m, 3H). BC NMR (125 MHz, DMSO-$d_6$) δ 167.2, 155.1, 154.0, 133.2, 133.1, 131.7, 131.1, 129.5, 123.5, 122.9. $^{11}$B NMR (128 MHz, DMSO-$d_6$) 28.6. IR(cm$^{-1}$) 3395 (br), 3106, 3064, 2359, 2339, 2161, 1682, 1601. LRMS m/z expected for $C_{13}H_{10}BN_2O_4$ [M+H]$^-$ 269.07, measured 269.1.

(E)-4-((4-(4,4,5,5-tetramethyl-1,3,2-dioxaborolan-2-yl)phenyl)diazenyl)benzoate (SI-3)

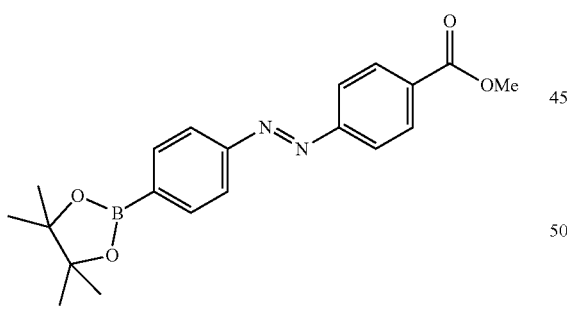

SI-1 (1.1 g, 6.60 mmol) and 4-(4,4,5,5-tetramethyl-1,3,2-dioxaborolan-2-yl)aniline (1.6 g, 7.3 mmol) were dissolved in DCM (100 mL) in a 200 mL RBF. Acetic acid (5 mL) was added dropwise. Initially the solution was neon green, but over the course of 24 hours the reaction turned dark red. Upon completion, the reaction was extracted against water (1×), 1M HCl (1×), and brine (1×). The combined organics were concentrated in vacuo and dissolved in DCM, which was passed through a silica plug and concentrated in vacuo. The resulting product was recrystallized from 9:1 hexane:EtOAc to provide the title product (712 mg, 30%). $^1$H NMR (500 MHz, CDCl$_3$) δ 8.20 (d, J=8.6 Hz, 2H), 8.01-7.95 (m, 4H), 7.93 (d, J=8.3 Hz, 2H), 3.96 (s, 3H), 1.38 (s, 12H). $^{13}$C NMR (125 MHz, CDCl$_3$) δ 166.5, 155.2, 154.2, 135.7, 131.9, 130.6, 122.7, 122.2, 84.2, 52.4, 24.9. $^{11}$B NMR (128 MHz, CDCl$_3$) 30.1. IR(cm$^{-1}$) 2978, 2956, 2928, 2361, 2343, 1716, 1601. HRMS: m/z expected for $C_{20}H_{24}BN_2O_4$ [M+H]$^+$ 367.18, measured 367.18.

(E)-(4-((4-(methoxycarbonyl)phenyl)diazenyl)phenyl)boronic acid (SI-4)

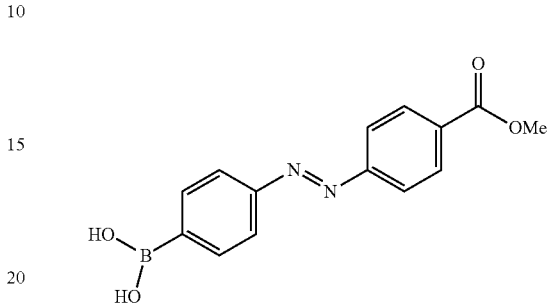

SI-3 (510 mg, 1.39 mmol) was dissolved in 25 mL of THF into a 100 mL RBF equipped with a stir bar to give a red-colored solution. Sodium periodate (298 mg, 1.39 mmol) was dissolved in water (6.2 mL) and added to the reaction. After 30 minutes, 1 mL of 1 M HCl was added to the solution, which was stirred for a further 6 hours. Upon full conversion, the THF was removed in vacuo, leading to the precipitation of the product, which was collected on a glass frit. The solids were washed with water (3×10 mL) and acetonitrile (10 mL) and dried to provide the title product (320 mg, 81%) as a peach-colored solid. $^1$H NMR (500 MHz, DMSO-$d_6$) δ 8.30 (s, 2H), 8.18 (d, J=8.2 Hz, 2H), 8.05-7.99 (m, 4H), 7.90 (d, J=7.9 Hz, 2H), 3.92 (s, 3H). $^{13}$C NMR (125 MHz, DMSO-$d_6$) δ 166.1, 154.5.0, 153.4, 135.7, 132.1, 131.0, 123.2, 122.2, 52.9. $^{11}$B NMR (128 MHz, DMSO-$d_6$) 26.8. IR (cm$^{-1}$) 3346 (br), 2965, 2358, 1724, 1604. HRMS m/z expected for $C_{14}H_{14}BN_2O_4$ [M+H]$^+$ 285.10, measured 285.10.

(E)-4-((4-boronophenyl)diazenyl)benzoic acid (SI-5)

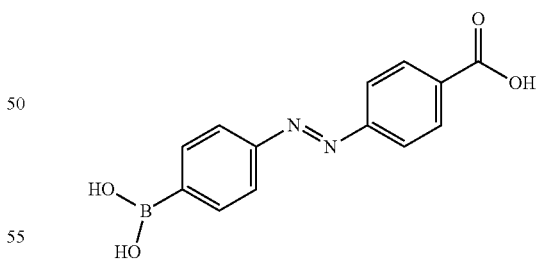

SI-4 (1.19 g, 4.19 mmol) was dissolved in methanol (112 mL) in a 250-mL RBF equipped with a stir bar. Lithium hydroxide (0.401 g, 16.8 mmol) was dissolved in water (23 mL) and added to the solution, which was stirred overnight. After 14 hours, the reaction was as an orange solution. The methanol was removed in vacuo and then 1M NaOH was added to the crude mixture to dissolve the solids. The aqueous solution was washed with EtOAc and then neutralized with 1M HCl, leading to the precipitation of the product. The solids were filtered, washed with water, and dried to provide the title product (160 mg, 50%) as a peach-colored solid. ¹H NMR (500 MHz, DMSO-d₆) δ 8.10 (d, J=8.2 Hz, 2H), 7.99 (d, J=7.9 Hz, 2H), 7.89 (d, J=8.1 Hz, 2H), 7.86 (d, J=8.1 Hz, 2H). ¹³C NMR (125 MHz, DMSO-d₆) δ 168.7, 1538, 153.5, 138.3, 135.6, 130.8, 122.6, 122.0. ¹¹B NMR (128 MHz, DMSO-d₆) 26.5. IR (cm⁻¹) 3406 (br), 2359, 1692, 1601. HRMS m/z expected for $C_{13}H_{10}BN_2O_4$ [M+H]⁻ 269.07, measured 269.07.

4-amino-3,5-difluorobenzoic acid

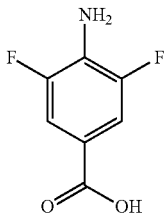 [SMILES: Nc1c(F)cc(C(=O)O)cc1F]

4-Amino-3,5-difluorobenzoic acid was synthesized by following a previously reported procedure. Characterization data were consistent with literature reports. (Bléger, D. et al., *J. Am. Chem. Soc.* 2012, 134, 20597.)

Methyl 4-amino-3,5-difluorobenzoate (SI-6)

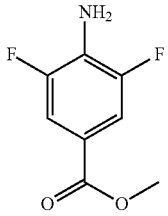

4-Amino-3,5-difluorobenzoic acid (500 mg, 2.89 mmol) was dissolved in 20 mL of MeOH, to which 1.75 mL of concentrated sulfuric acid was added. The reaction was heated to reflux for 14 hours. After the reaction, the solvent was removed in vacuo and 20 mL of water was added, leading to the precipitation of the product, which was collected and dried on a funnel to provide the title product (417 mg, 77%) as a white solid, which was used in the next reaction without further purification. ¹H NMR (500 MHz, CDCl₃) δ 7.58-7.46 (m, 2H), 4.14 (s, 2H), 3.87 (s, 3H).

Methyl 3,5-difluoro-4-nitrosobenzoate (SI-7)

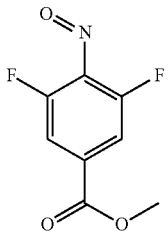

Methyl 4-amino-3,5-difluorobenzoate (2.52 g, 13.5 mmol) was dissolved in DCM (60 mL) into a 500 mL RBF equipped with a stir bar, and oxone (30.2 g, 49.1 mmol) in water (240 mL) was added to the solution, which was left to react for 24 hours. The organic layer was washed with 1M HCl (1×), 1M NaOH (1×), and DI water (1×). This was concentrated to give the title product (2.05 g, 76%) as a yellow solid, which was used in the next reaction without further purification.

(E)-(2-((2,6-difluoro-4-(methoxycarbonyl)phenyl)diazenyl)phenyl)boronic acid (SI-8)

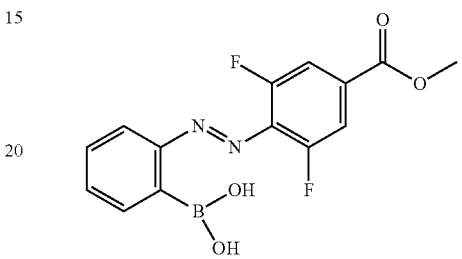

SI-7 and 2-(4,4,5,5-tetramethyl-1,3,2-dioxaborolan-2-yl)aniline (2.23 g, 10.2 mmol) were weighed into a 100 mL RBF equipped with a stir rod under inert atmosphere. DCM (70 mL) was added, and the dissolution of both starting materials led to the development of a dark-colored solution. Acetic acid (12 mL) was added, and the solution was left to react for 24 hours. After 24 hours, the solvent was removed in vacuo and with high vacuum (to remove excess acetic acid), and the crude residue was diluted in 100 mL of hexane and filtered to provide the protected crude (2.17 g) as a red solid. This material was dissolved in 130 mL of THF into a 250 mL RBF equipped with a stir rod. Sodium periodate (3.46 g, 16.2 mmol) was added in 30 mL of water, and the solution was left to react for 14 hours. After the reaction, the THF was removed in vacuo, and the remaining crude was diluted with 100 mL of DCM. The product precipitated from solution and was collected on a Buchner funnel, which was washed with an additional 100 mL of DCM to yield the title product (1.12 g, 34%) as a dark orange solid. ¹H NMR (500 MHz, DMSO-d₆) δ 7.99 (s, 2H), 7.87-7.80 (m, 3H), 7.71-7.67 (m, 1H), 7.63-7.57 (m, 2H), 3.92 (s, 3H). ¹³C NMR (125 MHz, DMSO-d₆) δ 164.2, 156.1, 156.0, 154.1, 134.2, 132.9, 130.2, 120.5, 114.4, 114.2, 53.5 ¹⁹F NMR (#MHz, DMSO-d₆) δ −116.6 (E), −119.8 (Z) IR (cm⁻¹) 3266 (br), 2361, 1724, 1592. LRMS m/z expected for $C_{14}H_{11}BF_2N_2O_4$ [M+H]⁺ 321.08, measured 321.1.

(E)-4-((2-boronophenyl)diazenyl)-3,5-difluorobenzoic acid (SI-9)

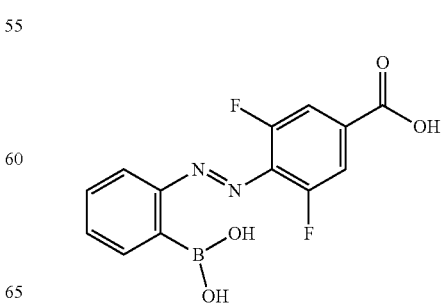

SI-8 (70 mg, 0.22 mmol) was dissolved in 7 mL of MeOH into a 25 mL RBF equipped with a stir bar, to which LiOH (16 mg, 0.66 mmol) in 3 mL of water was added. The reaction was left to react for 14 hours. After the reaction, the methanol was removed in vacuo and the water was neutralized with 1M HCl, leading to the precipitation of the product. The product was dissolved in EtOAc and washed with water. The organic layer was dried with sodium sulfate and then concentrated in vacuo to give the title product (64.4 mg, 96%) as an orange solid. $^1$H NMR (500 MHz, DMSO-$d_6$) δ 7.99 (s, 2H), 7.83 (d, J=7.4 Hz, 1H), 7.79 (d, J=9.5 Hz, 2H), 7.69 (s, 1H), 7.60 (tt, J=7.3, 5.6 Hz, 2H) $^{13}$C NMR (125 MHz, DMSO-$d_6$) δ 165.2, 156.1, 156.0, 154.1, 134.2, 132.8, 130.2, 120.2, 114.3, 114.1 $^{19}$F NMR (#MHz, DMSO-$d_6$) δ −117.0 (E), −120.1 (Z) IR (cm$^{-1}$) 3361 (br), 3053, 2358, 1720, 1595. LRMS m/z expected for $C_{13}H_9BF_2N_2O_4$ [M+H]$^+$ 306.06, measured 307.0.

Small-Molecule Kinetics

Procedure for Calibration Curves

Stock solutions of (E)-1 or (E)-2 were prepared in acetonitrile at 800 μM. Serial dilutions were performed to obtain a final concentration of 12.5 μM. The solutions were directly injected onto the LCMS (Poroshell 120 column, EC-C18, 2.7 μm, 2.1×50 mm). Runs were ten minutes long with solvent gradient from 50:50 to 100:0 ACN:H$_2$O in the first three minutes. Detection was performed at 254 nm with a variable-wavelength detector. The peak area for each concentration was recorded. A calibration curve was created. The Z-isomer calibration curves were prepared by irradiating the series above for 10 minutes with 365 nm UV light and directly injecting the solution onto the LCMS. The concentration of the Z-isomer can be calculated from the known concentration of the E-isomer (based on the previously-generated calibration curve).

Pseudo-First Order Reversible Esterification of (E)-1

500 μL of a stock solution of 800 μM of (E)-1 was diluted with 500 μL of 80 mM of pinacol in DI water. The concentrations of (E)-1 and (E)-2 were monitored as a function of time using the above LCMS method. The observed rate constants of esterification ($k_{1(E)}$) and hydrolysis ($k_{-1(E)}$) were determined using the derivation shown below.

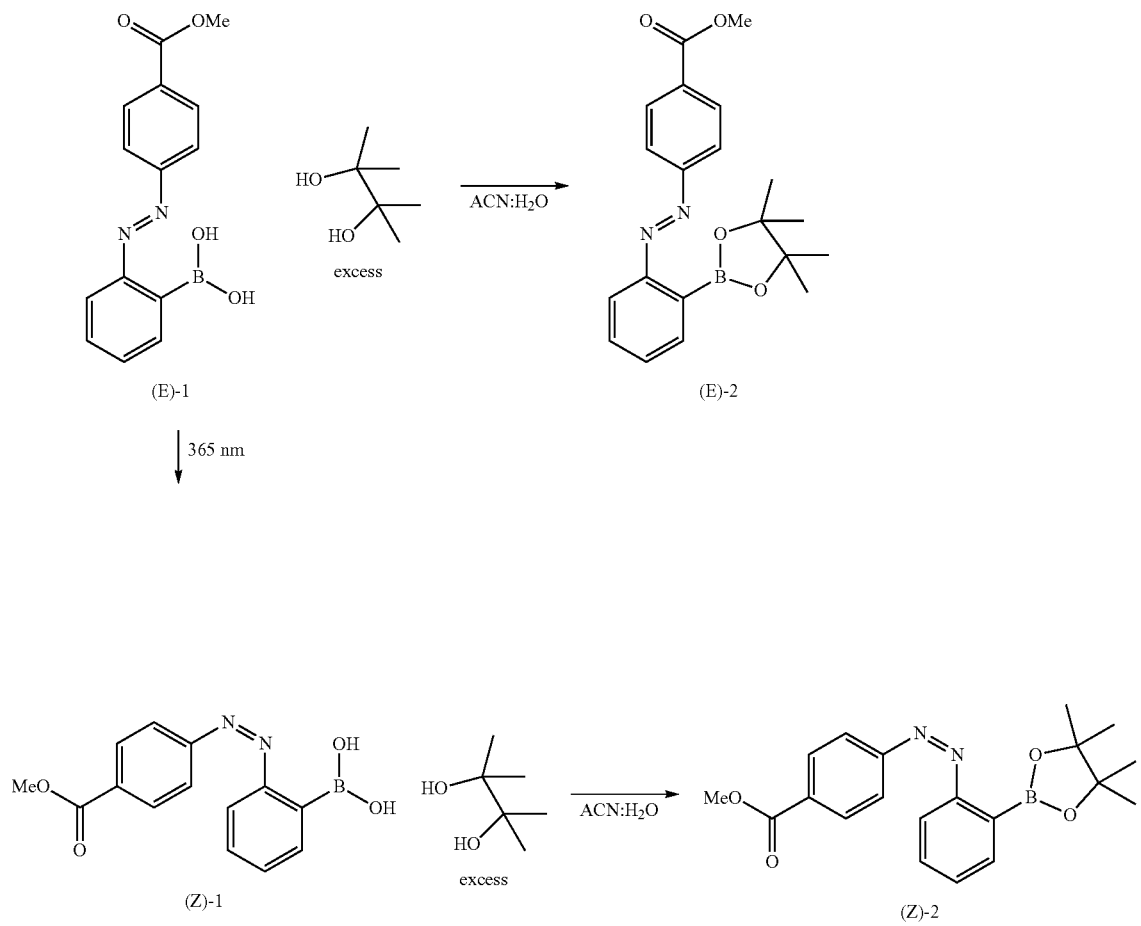

Scheme S2. Chemical structures for the pseudo-first order reversible esterification of (E)-1 and/or (Z)-1. The photochemical E/Z isomerization is drawn as irreversible due to the slow thermal relaxation of (Z)-1 and (Z)-2. This also allows for the simplification of the derivation of observed rate constants, shown below.

The data from the concentrations vs. time experiments was fit to the linear expression (1) for a reversible first order reaction and yields the slope denoted as equation (4). (Bléger, D. et al., 2012.) The apparent equilibrium constant for the reaction is the ratio of (E)-2 to (E)-1 when the reaction comes to equilibrium, which can also be represented as equation (2) and rewritten as equation (3). With the apparent equilibrium constant and slope known, the rates of hydrolysis can be determined with equation (5), and subsequently the rate of esterification can be determined.

$$\ln([(E)-2]_e - \ln[(E)-2]_t) - \ln([(E)-2]_e - \ln[(E)-2]_0) = \qquad (1)$$
$$(k'_{1(E)} - k'_{-1(E)})t$$

where $k'_{-1(E)} = k_{-1(E)}[H_2O]$ and $k'_{1(E)} = k_{1(E)}[(E)-1]$ $$K'_{eq(E)} = \frac{k'_{1(E)}}{k'_{-1(E)}} \qquad (2)$$

$$k'_{-1(E)} K'_{eq(E)} = k'_{1(E)} \qquad (3)$$

$$k'_{-1(E)} + k'_{1(E)} = \text{slope} \qquad (4)$$

$$k'_{-1(E)} = \frac{\text{slope}}{1 + K'_{eq(E)}} \qquad (5)$$

Pseudo-First Order Reversible Esterification of (Z)-1 and (E)-1

500 µL of a stock solution of 800 µM of (E)-1 was irradiated with a 365 nm flashlight for 10 minutes to produce a mixture of (E)-1 and (Z)-1. The mixture was then diluted with 500 µL of a 80 mM pinacol solution in DI water, and the concentrations of (E)-2 and (Z)-2 were monitored as a function of time using the above LCMS method. The observed rate constants of esterification and hydrolysis $k_{1(Z)}$ and $k_{-1(Z)}$ were solved for using the same derivation as shown for the E isomer. A small increase in the total concentrations of (E)-1 and (E)-2 over the course of this experiment were ascribed to thermal relaxation of the (Z) isomers.

Pseudo-First Order Irreversible Hydrolysis of (Z)-2 and (E)-2

500 µL of a stock solution of 800 µM of (E)-2 was irradiated with a 365 nm flashlight for 10 minutes to produce a mixture of (E)-2 and (Z)-2. The mixture was then diluted with 500 µL of DI $H_2O$ and the concentration of (E)-2 and (Z)-2 was monitored as a function of time. The observed rate constants of hydrolysis $k_{-1(E)}$ and $k_{-1(Z)}$ were determined using the derivation shown below.

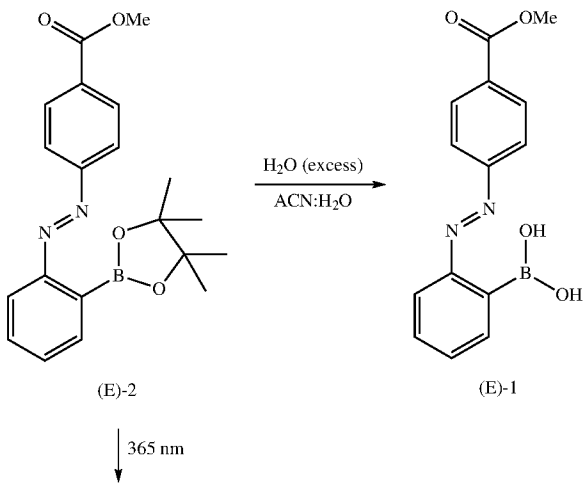

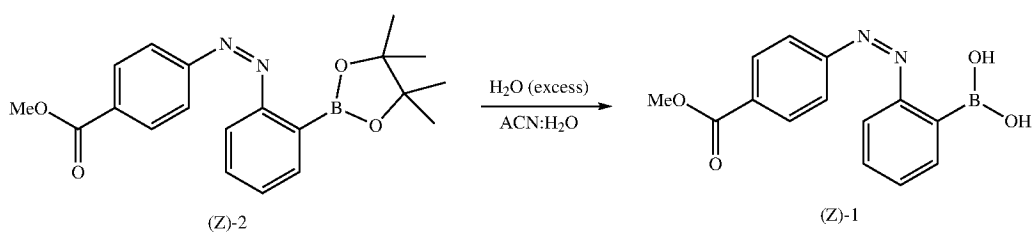

Scheme S3. Chemical structures for the pseudo-first order irreversible hydrolysis of (E)-2 and/or (Z)-2. The photochemical E/Z isomerization is drawn as irreversible due to the slow thermal relaxation of (Z)-1 and (Z)-2. This also allows for the simplification of the derivation of observed rate constants, shown below.

The concentrations vs. time can be fit to the linear expression (6) for an irreversible first order reaction where the slope is the apparent rate constant for the respective isomer. (Hartley, F. R., Chem. Br. 1984, 20, 148.)

$$\ln[(E)\text{-}2]_t - \ln[(E)\text{-}2]_0 = -k'_{-1(E)} t \quad (6)$$

where $k'_{-1(E)} = k_{-1(E)}[H_2O]$

Functionalization of 4-Arm PEG

P1 was prepared following a literature procedure. (Yesilyurt, V. et al., Adv. Mater. 2016, 28, 86.)

P2 was synthesized based on an adapted literature procedure. (Yesilyurt, V. et al, Adv. Mater. 2017, 29.) 500 mg of 4-arm PEG amine HCl salt ($M_w$ 5000) was added to a Schlenk flask (50 mL) and melted under high vacuum (3×) to remove excess water. HOBt (0.2 g, 1 mmol), benzotriazol-1-yloxytris(dimethylamino)-phosphonium hexafluorophosphate (0.4 g, 1 mmol), and SI-2 (0.3 g, 1 mmol) were then added as solids along with a stir bar. The vessel was sealed and backfilled with nitrogen three times. 5 mL of DCM and 5 mL of dimethylformamide (DMF) were then added to solubilize the reagents, leading to a clear red solution. Triethylamine (91 mg, 125 μL, 0.90 mmol) was added to the solution, which was stirred at room temperature for 24 hours. The solvent was removed in vacuo, and the solution was diluted with DI water to form an orange precipitate. The solids were removed by filtration using a fritted funnel, and the aqueous orange filtrate was subject to dialysis (MWCO=3.5 kDa) against DI water for 24 hours, during which time the dialysate was changed at least 3 times. After dialysis, the sample was lyophilized for 48 hours, yielding 320 mg of an orange powder, P2. Polymers should be stored dry in fridge without exposure to light to preserve integrity. Leaving solutions of P2 in DI water in ambient light for 24 hours leads to protodeboronation, as evinced by proton NMR.

P2-$F_2$ was prepared using the same procedure as P2, using SI-10. After dialysis, this solution was concentrated and purified using a spin filter (MWCO=5 KDa). After the reaction, it was lyophilized for 48 hours (91 mg yield).

P3 was synthesized by the same procedure as P2, using SI-5 (377 mg yield).

P4 was synthesized by same procedure as P2, using (E)-4-(phenyldiazenyl)benzoic acid (217 mg yield).

Rheology

Mechanical characterization of the prepared hydrogels was performed using an Anton Paar MCR 302 Rheometer with a 25 mm, 5° cone-plate attachment. 10% strain was established to be within the linear viscoelastic regime for all time points tested. Unless noted otherwise, oscillatory strain amplitude sweeps were conducted using a frequency of 25 rad/s, and oscillatory frequencies were conducted using 10% strain. Gelation profiles were conducted with 10% strain and a frequency of 25 rad/s. Frequency sweeps were performed at 10% strain, with a frequency range of 300 to 1 rad/s. Data were collected at 25° C. Gels were prepared by mixing 200l of P1 (10 w/v % in 0.1M PBS, pH 7.5) with P2, P3, or P4 (10 w/v % in 0.1M PBS, pH 7.5).

A consistent observation from the reversible gelation profiles is that the first stiffening event occurred approximately twice as slowly compared to subsequent cycles. This may be due to (a) a slightly elevated temperature of the glass plate of the photorheology setup after continuous irradiation, (b) diffusion processes in the macroscopic gel, or (c) the photostationary state after blue irradiation was <100% E isomer. While it was not possible to control this temperature apart from implementation of a fan, no more than a 3° C. increase in temperature was observed at the sample as measured by as measure by a fluke 62 max IR thermometer.

TABLE 2

Tabulated data of low frequency crossover points and respective modulus (Pa) of gels prepared from P1 and P2 (1:1, 10 w/v % in 0.1M PBS, pH 7.5, 10% strain) at different irradiation intervals.

| Time Irradiated at 365 nm | $\omega_c$ | G at $\omega_c$ |
|---|---|---|
| 20 | 7.49 | 5.94 |
| 40 | 7.98 | 11 |
| 60 | 8.1 | 17.5 |
| 90 | 7.78 | 32.2 |
| 120 | 7.45 | 47.5 |
| 180 | 7.11 | 84.3 |
| 240 | 7.75 | 141 |

Example 2: Alginate-Based Hydrogels

A ring opening reaction between δ-gluconolactone and sodium alginate, a polysaccharide commonly used in biomaterials, was used to form a water-soluble, unhindered penta-ol-grafted polymer (FIG. 11A). The grafted alginate formed photoresponsive gels in combination with a telechelic bis-azobenzene boronic acid having ortho-fluorine atoms on the arylboronic acid ring as a linker.

The alginate-based gels exhibited reversibly photocontrolled stiffness (with a maximum stiffness of 9 kPa (FIG. 11B). The alginate-based gels displayed significantly slower stress relaxation than PEG-based gels (FIG. 11C). However, as in the PEG gels, the stress relaxation of alginate gels was constant as a function of irradiation and stiffness.

Example 3: Hybrid Collagen/Poly(ethylene glycol)-Based Interpenetrating Network 5 mg of P1 (10 kDa-8 arm) and 5 mg P2-$F_2$ (5 kDa, 4-arm) were added to a solution of 20 μL of 10×PBS, 2.8 μL of 1M NaOH, 57.2 μL of deionized water, and 48 μL of 20 mM acetic acid. 72 μL of stock collagen solution was added to this and fibrillogensis was set in the solution state by incubating the gel for 30 minutes at 37° C. Rheological data was collected at 10% strain and 25 rad/s.

Example 4: Hybrid ECM/Poly(ethylene glycol)-Based Interpenetrating Network

A 20 w/v % stock solution of P2-$F_2$-5 kDa was prepared in deionized water and a 20 w/v % stock solution of P1-5 kDa was prepared in 2×PBS buffer (pH 7.4). 50 μL of P1 solution and 50 μL of P2-$F_2$ solution were combined with 100 μL of 10×PBS pH (7.5 s) and then added to 100 μL decellularized rat liver ECM (5 w/v %, neutralized) that had been gelled for 30 min at 37° C. Rheological data were collected at 10% strain and 25 rad/s.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A reversibly crosslinkable composition comprising:
   a first molecule comprising at least two terminal azobenzene boronic acid groups; and
   a second molecule comprising at least two terminal diol groups, wherein at least one of the first and second molecules is a polymer, and further wherein, if the first molecule has only two terminal azobenzene boronic acid groups, then the second molecule comprises at least three terminal diol groups, and if the second molecule has only two terminal diol groups, the first molecule has at least three terminal azobenzene boronic acid groups;
   wherein the first molecule is characterized in that its azobenzene groups undergo a reversible E to Z isomerization upon irradiation with ultraviolet light, visible light, or infrared light, and its boronic acid groups react with the terminal diol groups of the second polymer to form a polymer network comprising covalent azobenzene boronic ester bonds.

2. The composition of claim 1, wherein one or both of the first molecule and the second molecule comprise polysaccharide chains.

3. The composition of claim 2, wherein the polysaccharide chains comprise hyaluronic acid chains.

4. The composition of claim 1, wherein one or both of the first molecule and the second molecule comprise poly(ethylene glycol) chains.

5. The composition of claim 1, wherein one or both of the first molecule and the second molecule comprise decellularized extracellular matrix.

6. The composition of claim 1, wherein one or both of the first molecule and the second molecule comprise fiber-forming components of extracellular matrix.

7. The composition of claim 1, wherein one or both of the first molecule and the second molecule comprise alginate chains.

8. The composition of claim 1, wherein the azobenzene groups are ortho-difluoroazobenzene groups.

9. The composition of claim 1, wherein the azobenzene groups comprise an electron withdrawing group para to the boronic ester group.

10. A method of inducing a reversible polymer network formation in a reversibly crosslinkable composition comprising:
    a first molecule comprising at least two terminal azobenzene boronic acid groups; and
    a second molecule comprising at least two terminal diol groups, wherein at least one of the first and second molecules is a polymer, and further wherein, if the first molecule has only two terminal azobenzene boronic acid groups, then the second molecule comprises at least three terminal diol groups, and if the second molecule has only two terminal diol groups, the first molecule has at least three terminal azobenzene boronic acid groups;
    wherein the first molecule is characterized in that its azobenzene groups undergo a reversible E to Z isomerization upon irradiation with ultraviolet light, visible light, or infrared light, and its boronic acid groups react with the terminal diol groups of the second polymer to form a polymer network comprising covalent azobenzene boronic ester bonds,
    the method comprising:
    irradiating at least a portion of the composition with ultraviolet light, visible light, or infrared light that induces the azobenzene groups of the first molecule to undergo a reversible E to Z isomerization, whereby its boronic acid groups react with the terminal diol groups of the second molecule to form a polymer network comprising covalent azobenzene boronic ester bonds.

11. The method of claim 10, further comprising removing one or more portions of the composition that were not irradiated by the ultraviolet light, visible light, or infrared light.

12. The method of claim 10, further comprising irradiating at least a portion of the polymer network with visible light that induces the azobenzene groups of the first polymer to undergo a reversible Z to E isomerization, whereby azobenzene boronic ester bonds in the polymer network are broken.

13. The method of claim 10, wherein two or more different regions of the composition are irradiated with the ultraviolet light, visible light, or infrared light for different time durations, at different light intensities, or at different wavelengths of light, such that the two or more different regions of the polymer network have different stiffness properties.

14. The method of claim 10, wherein a first region of the two or more different regions of the composition has a $G'_{max}$ that is at least twice the $G'_{max}$ of a second of the two or more different regions of the composition.

15. The method of claim 10, further comprising seeding the polymer network with living biological cells.

16. The method of claim 15, further comprising culturing the biological cell-seeded polymer network in a cell growth culture medium.

17. The method of claim 10, wherein the polymer network comprises polysaccharide chains.

18. The method of claim 17, wherein the polysaccharide chains comprise hyaluronic acid chains.

19. The method of claim 10, wherein the polymer network comprises poly(ethylene glycol) chains.

* * * * *